(12) United States Patent
Gyuris et al.

(10) Patent No.: US 6,420,110 B1
(45) Date of Patent: Jul. 16, 2002

(54) METHODS AND REAGENTS FOR ISOLATING BIOLOGICALLY ACTIVE PEPTIDES

(75) Inventors: Jeno Gyuris, Winchester; Aaron J. Morris, Boston, both of MA (US)

(73) Assignee: GPC Biotech, Inc., Waltham, MA (US)

( * ) Notice: Subject to any disclaimer, the term of this patent is extended or adjusted under 35 U.S.C. 154(b) by 0 days.

(21) Appl. No.: 09/174,943

(22) Filed: Oct. 19, 1998

(51) Int. Cl.$^7$ .......................... C12Q 1/70; G01N 33/53; C12P 21/06; C12N 7/00

(52) U.S. Cl. .............................. 435/6; 435/5; 435/7.1; 435/69.1; 435/235.1; 435/DIG. 1; 435/DIG. 3; 435/DIG. 4; 435/DIG. 15

(58) Field of Search ..................... 435/7.2, 6, 4, DIG. 4, 435/DIG. 3, DIG. 2, DIG. 15, DIG. 14, 5, 7.1, 235.1, 69.1

(56) References Cited

U.S. PATENT DOCUMENTS

| | | | |
|---|---|---|---|
| 5,222,409 A | 6/1993 | Dalakian | 74/479 R |
| 5,223,409 A | 6/1993 | Ladner et al. | 435/69.7 |
| 5,580,717 A | * 12/1996 | Dower et al. | 435/5 |

FOREIGN PATENT DOCUMENTS

| | | |
|---|---|---|
| WO | WO 90/02809 | 3/1990 |
| WO | WO 91/17271 | 11/1991 |
| WO | WO 92/01047 | 1/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | WO 95/34648 | 12/1995 |
| WO | WO 98/47343 | 10/1998 |
| WO | WO 99/25818 | 5/1999 |

OTHER PUBLICATIONS

Szoka et al, DNA, 5(1), (1986), 11–20.*
Nakashima et al, The Jounl. of Biol. Chem., 256 (11), (Jun. 10, 1981), 5792–5797.*
Cabonilly, Methods in Mol. Biol., 87, 129–136*
Christian et al, J. Mol. Bol., (1992), 227, 711–18.*
Scott, TIB, (1992), 241–245.*
Pansch, TIBTECH (12/97), 15, 487–494.*
Atwell, S. et al. "Stable heterodimers from remodeling the domain Interface of a homodimer using a phage display library" *J. Mol. Biol.,* 270, Apr. 25, 1997, 26–35.
Barbas III et al., "Semisynthetic Combinatorial Antibody Libraries : A Chemical Solution to the Diversity Problem", Proc. Natl. Acad. Sci. USA 89:4457–4461 (May 1992).
Barbas III et al., "Assembly of Combinatorial Antibody Libraries on Phage Surfaces: The Gene III site", Proc. Natl. Acad. Sci. USA 88: 7978–7982 (1991).

Charbit et al, "Versatility of a Vector for Expressing Foreign Polypeptides at the Surface of Gram–Negative Bacteria", Gene, 70:181–189 (1988).
Clarckson et al., "Making Antibody Fragments Using Phage Display Libraries", Nature 352: 624–628 (Aug. 1991).
Cull et al., "Screening For Receptor Ligands Using Large Libraries of Peptides Linked to the C Terminus of the Lac Repressor", Proc. Natl. Acad. Sci. USA, 89: 1865–1869 (Mar. 1992).
Cwirla et al., "Peptides on Phage: A Vast Library of Peptides for Identifying Ligands", Proc. Natl. Acad. Sci. USA, 87:6378–6382 (Aug. 1990).
De la Cruz et al., "Immunogeniticity and Epitope Mapping of Foreign Sequences Via Genetically Engineered Filamentous Phage", The Journal of Biological Chemistry, 263 (9): 4318–4322 (1988).
Dower et al., "High Efficiency Transformation of *E. coli* by High Voltage Electroporation", Nucleic Acids Research, 16(13):6127–6145 (1988).
Fuchs et al., "Targeting Recombinant Antibodies to the Surface of *Escherichia Coli*: Fusion to a Peptidoglycan Associated Lipoprotein", Bio/technology, 9: 1369–1372 (Dec. 1991).
Garrard [1] et al., "$F_{AB}$ Assembly Enrichment in a Monovalent Phage Display System", Bio/technology, 9:1373–1377(Dec. 1991).
Gram et al., "In Vitro Selection and Affinity Maturation of Antibodies from a Naive Combinatorial Immunoglobulin Library", Proc. Natl. Acad. Sci. USA 89:3576–3580 (Apr. 1992).
Griffiths [1]et al., "Human Anti–Self Antibodies With High Specificity From Phage Display Libraries", The Embo Journal, 12 (2): 725–734 (1993).
Hoogenboom [1] et al., "Multi–/Subunit Proteins on the Surface of Filamentous Phage: Methodologies for Displaying Antibody (Fab) Heavy and Light Chains", Nucleic Acids Research, 19(15): 4133–4137 (1991).
Huse et al., "Generation of a Large Combinatorial Library of the Immunoglobulin Repertoire in Phage Lambda", Science, 246:1275–1281(Dec. 8, 1989).
Marks et al., "Molecular Evolution of Proteins on Filamentous Phage: Mimicking The Strategy of the Immune System", The Journal of Biological Chemistry 267(23):16007–16010 (Aug. 15, 1992).

(List continued on next page.)

*Primary Examiner*—Padmashri Ponnaluri
(74) *Attorney, Agent, or Firm*—Ropes & Gray; Matthew P. Vincent; David P. Halstead

(57) ABSTRACT

One aspect of the present invention is the synthesis of a binary method that combines variegated peptide display libraries, e.g., in a "display mode", with soluble secreted peptide libraries, e.g., in a "secretion mode", to yield a method for the efficient isolation of peptides having a desired biological activity.

42 Claims, 14 Drawing Sheets

OTHER PUBLICATIONS

Mattheakis et al., An In Vitro Polysome Display System for Identifying Ligands From very Large Peptide Libraries', Proc Natl. Acad. Sci. USA, 91:9022–9028 (Sep. 1994).

Mullinax et al., Identification of Human Antibody Fragment Clones Specific for Tetanus Toxoid in a Bacteriophage λ Immunoexpression Library', Proc. Natl. Acad. Sci. USA, 87:8095–8099 (Oct. 1990).

Parmley and Smith., "Antibody–Selectable Filamentous fd Phage Vectors : Affinity Purification of Target Genes", Gene, 73:305–318 (1988).

Persson et al., "Generation of Diverse High–affinity Human Monoclonal Antibodies by Repertoire Cloning", Proc. Natl. Acad. Sci. USA, 88:2432–2436 (Mar. 1991).

Randall et al., "Export of Protein: A Biochemical View", Ann. Rev. Microbiol., 41:507–541 (1987).

Ronco et al., "Creation of Targets for Proteolytic Cleavage in the LamB Protein of *E coli* K12 by genetic insertion of foreign sequences : Implications for topological studies", Biochimie 72:183–189(1990).

Scott and Smith., "Searching for Peptide Ligands with an Epitope Library", science, 249:386–390 (Jul. 27, 1990).

Smith P. George., "Filamentous Fusion Phage: Novel Expression Vectors That Display Cloned Antigens on the Virion Surface", Science, 228:1315–1317(Jun. 14, 1985).

Young and Davis., Yeast RNA Polymerase II Genes: Isolation with Antibody Probes', Science 222: 778–782(Nov. 18, 1983).

\* cited by examiner

Characterization of the peptide display vectors

| Plasmids: | c.f.u.: | p.f.u.: | c.f.u./p.f.u.: |
|---|---|---|---|
| pAM6 | $2.8 \times 10^{12}$/ml | $1.9 \times 10^{11}$/ml | ~15 |
| pAM7 | $2 \times 10^{12}$/ml | $1.5 \times 10^{11}$/ml | ~13 |
| pAM8 | $10^{12}$/ml | $2.2 \times 10^{11}$/ml | ~5 |
| pLITMUS | $2 \times 10^{12}$/ml | $8.4 \times 10^{11}$/ml | ~2 |

METHODS AND REAGENTS FOR ISOLATING BIOLOGICALLY ACTIVE PEPTIDES

BACKGROUND OF THE INVENTION

High throughput screening has become a dominant tool in the pharmaceutical industry for the discovery of lead compounds that can be modified into candidates for drug development. For instance, it is abundantly used for identification of ligands with high affinity for receptors. In this regard, combinatorial techniques have provided approaches to generating and deconvoluting large libraries of test compounds in high throughput screens. It involves selection and amplification of a subset of molecules with desired biological properties from complex libraries.

One technique which has emerged for identification of peptide leads involves the use of peptide display methodologies such as phage display. Phage-displayed peptide libraries can comprise vast collections of short, randomized polypeptides that are displayed on the surface of a filamentous bacteriophage particle. Thus, each "peptide" is actually the N-terminal sequence of a phage-coat protein, that is encoded by a randomly-mutated region of the phage genome responsible for the production of the coat protein. In this manner, each unique peptide in the library is physically linked with the DNA molecule encoding it. Antibodies and other binding molecules can be used as "targets" to specifically select rare phage clones bearing ligand peptides, and sequencing of the corresponding viral DNA will reveal their amino acid sequences. Relatively high-affinity peptides for a variety of peptide- and non-peptide-binding targets have been affinity-isolated from epitope libraries. This technology has been used to map epitopes on proteins and to find peptide mimics for a variety of target molecules. Many powerful applications can be envisioned in the areas of drug design and the development of diagnostic markers, vaccines and toleragens.

For the purposes of drug discovery, there are potential advantages in the use of genetically encoded libraries, such as phage display (Scott et al, *Science* 249, 386 (1990); Devlin et al., *Science* 249, 386 (1990)), "peptide on plasmid" (Cull et al. *PNAS* 89, 1865 (1992)), and in vitro translation-based systems (Mattheakis et al. *PNAS* 91, 9022 (1994)), compared to the use of synthetic small molecule libraries (Bunin et al. *PNAS* 91, 4708 (1994); Gordon et al. *J. Med. Chem.* 37, 1385 (1994); and Dooley et al., *Science* 266, 2019 (1994)). The genetic encoding of libraries allows the resynthesis and rescreening of molecules with a desired binding activity. The resulting amplification of interacting molecules in subsequent rounds of selection can lead to the isolation of extremely rare, specific binders from a large pool of molecules.

However, despite the success of these methods, they suffer from numerous sources of error and bias, such as very low initial concentrations of species, non-specific binding, and, significantly, the sampling of only a fraction of the library at the end of an experiment.

SUMMARY OF THE INVENTION

One aspect of the invention provides a method for generating a peptide with a selected biological activity, comprising the steps of:

(i) providing a peptide display library comprising a variegated population of test peptides expressed on the surface of a population of display packages;

(ii) in a display mode, isolating, from the peptide display libary, a sub-population of display packages enriched for test peptides which have a desired binding specificity and/or affinity for a cell or a component thereof;

(iii) in a secretion mode, simultaneously expressing the enriched test peptide sub-population under conditions wherein the test peptides are secreted and are free of the display packages; and (iv) assessing the ability of the secreted test peptides to regulate a biological process in a target cell.

For instance, the peptide display library can be a phage display library, e.g., which utilizes phage particles such as M13, f1, fd, If1, Ike, Xf, Pf1, Pf3, λ, T4, T7, P2, P4, φX-174, MS2 or f2. In preferred embodiments, the phage display library is generated with a filamentous bacteriophage specific for *Escherichia coli* and the phage coat protein is coat protein III or coat protein VIII. For instance, the filamentous bacteriophage can be M13, fd, and f1.

In other embodiments, the peptide display library is a bacterial cell-surface display library or a spore display library.

In certain embodiments, the test peptides are enriched from the peptide display library in the display mode by a differential binding means comprising affinity separation of test peptides which specifically bind the cell or component thereof from test peptides which do not. For example, the differential binding means can include panning the peptide display library on whole cells, affinity chromatographic means in which a component of a cell is provided as part of an insoluble matrix (.e.g, a cell surface protein attached to a polymeric support), and/or immunoprecipitating the display packages.

In the display mode, the test peptides can be enriched for those which bind to a cell-type specific marker and/or a cell surface receptor protein. For example, the test peptide library can be enriched in the display mode for test peptides which bind to a G-protein coupled receptor, such as a chemoattractant peptide receptor, a neuropeptide receptor, a light receptor, a neurotransmitter receptor, a cyclic AMP receptor, or a polypeptide hormone receptor. In other embodiments, the test peptide library can be enriched in the display mode for test peptides which bind to a receptor tyrosine kinase, such as an EPH receptor. In still other embodiments, the test peptide library can be enriched in the display mode for test peptides which bind to a cytokine receptor or an MIRR receptor. In certain embodiments, the test peptide library can be enriched in the display mode for test peptides which bind to an orphan receptor.

In preferred embodiments, the peptide display library includes at least $10^3$ different test peptides.

In preferred embodiments, the test peptides are 4–20 amino acid residues in length.

In certain embodiments, each of the test peptides are encoded by a chimeric gene comprising (i) a coding sequence for the test peptide, (ii) a coding sequence for a surface protein of the display package for displaying the test peptides on the surface of a population of display packages, and (iii) RNA splice sites flanking the coding sequence for the surface protein, wherein, in the display mode, the chimeric gene is expressed as fusion protein including the test peptide and the surface protein, whereas in the secretion mode, the test peptide is expressed without the surface protein as a result of the coding sequence for the surface protein being removed by RNA splicing.

In preferred embodiments, the test peptides are expressed by a eukaryotic cell, more preferably a mammalian cell, in the secretion mode.

In preferred embodiments, the target cell is a eukaryotic cell, more preferably a mammalian cell such as a human cell.

In certain embodiments, the biological process scored for in the secretion mode includes a change in cell proliferation, cell differentiation or cell death. In other embodiments, the biological process which is detected is changes in intracellular calcium mobilization, intracellular protein phosphorylation, phospholipid metabolism, and/or expression of cell-specific marker genes.

In certain embodiments, the target cell includes a reporter gene construct containing a reporter gene in operative linkage with one or more transcriptional regulatory elements responsive to the signal transduction acitivity of the cell surface receptor protein, expression of the reporter gene providing the detectable signal. For instance, the reporter gene can encode a gene product that gives rise to a detectable signal selected from the group consisting of: color, fluorescence, luminescence, cell viability relief of a cell nutritional requirement, cell growth, and drug resistance. In preferred embodiments, the reporter gene encodes a gene product selected from the group consisting of chloramphenicol acetyl transferase, beta-galactosidase and secreted alkaline phosphatase. In other preferred embodiments, the reporter gene encodes a gene product which confers a growth signal.

In certain embodiments, the secretion mode includes assessing the ability of the secreted test peptides to inhibit the biological activity of an exogenously added compound on the target cells.

In an exemplary embodiment: in step (ii) above, display packages which bind to endothelial cells are isolated; and in step (iv) above, the ability of the secreted test peptides to inhibit proliferation of endothelial cells is assessed. For example, in step (iv) the ability of the secreted test peptides to inhibit proliferation of endothelial cells in the presense of an angiogenic amount of an endogenous growth factor can be assessed.

The subject invention also specifically contemplates that peptides identified in the secretion mode can be converted into peptidomimietics.

Moreover, in certain embodiments, the subject method includes the further step of formulating, with a pharmaceutically acceptable carrier, one or more test peptides which regulate the biological process in the target cell or peptidomimetics thereof.

Another aspect of the present invention provides a peptide display library enriched for test peptides having a desired binding specificity and/or affinity for a cell or a component thereof and which regulate a biological process in a target cell.

Still another aspect of the present invention relates to a vector comprising a chimeric gene for a chimeric protein, which chimeric gene comprises (i) a coding sequence for a test peptide, (ii) a coding sequence for a surface protein of a display package, and (iii) RNA splice sites flanking the coding sequence for the surface protein, wherein, in a display mode, the chimeric gene is expressed as a fusion protein including the test peptide and the surface protein such that the test peptide can be displayed on the surface of a population of display packages, whereas in the secretion mode, the test peptide is expressed without the surface protein as a result of the coding sequence for the surface protein being removed by RNA splicing.

In certain embodiments, the chimeric gene can include a secretion signal sequence for secretion of the test peptide in the secretion mode, e.g., secretion of the test peptide from eukaryotic cells, preferably mammalian cells.

Yet another aspect of the present invention provides a vector library, each vector comprising a chimeric gene for a chimeric protein, which chimeric gene comprises (i) a coding sequence for a test peptide, (ii) a coding sequence for a surface protein of a display package, and (iii) RNA splice sites flanking the coding sequence for the surface protein, wherein, in a display mode, the chimeric gene is expressed as fusion protein including the test peptide and the surface protein such that the test peptide can be displayed on the surface of a population of display packages, whereas in the secretion mode, the test peptide is expressed without the surface protein as a result of the coding sequence for the surface protein being removed by RNA splicing, the vector library collectively encodes a variegated population of test peptides.

In preferred embodiments, the vector library collectively encodes at least $10^3$ different test peptides.

In preferred embodiments, the test peptides are 4–20 amino acid residues in length.

Another aspect of the present invention is a cell composition comprising a population of cells containing the vector library described above.

Still another aspect of the present invention provides a method for generating a peptide with a selected antimicrobial activity, comprising the steps of:

(i) providing a recombinant host cell population which expresses a soluble peptide library comprising a variegated population of test peptides;

(ii) culturing the host cells with a target microorganism under conditions wherein the peptide library is secreted and diffuses to the target microorganism; and (iii) selected host cells expressing test peptides that inhibit growth of the target microorganism.

For example, the target microorganism is a bacteria or a fungus. In certain embodiments, the host cells are cultured on agar embedded with the target microorganisms. For example, antimicrobial activity of a test peptide can be determined by zone clearing in the agar.

DETAILED DESCRIPTION OF THE INVENTION

I. Overview

The present invention makes available a powerful directed approach for isolating biologically active peptides. One aspect of the present invention is the synthesis of a binary method that combines variegated peptide display libraries, e.g., in a "display mode", with soluble secreted peptide libraries, e.g., in a "secretion mode", to yield a method for the efficient isolation of peptides having a desired biological activity.

Utilizing peptide display techniques, a peptide library can first be reduced in complexity by panning or other affinity purification techniques. In particular, the subject method selects peptides having a certain affinity profile, e.g., a specificity and/or binding affinity for a discrete cell or protein or other cellular component thereof by (i) displaying the peptides on the outer surface of a replicable genetic display package to create a peptide display library, and (ii) using affinity selection techniques to enrich the population of display packages for those containing peptides which have a desired binding specificity for the target cell or cellular component (herein collectively referred to as the "target").

After the affinity enrichment step, the resulting sub-library is then utilized in a secretion mode whereby the test peptides are secreted as soluble extracellular factors and their effect as paracrine or autocrine factors is scored. That is, the secretion mode measures biological activity of the test peptides in order to distinguish between agonist, antagonist, and inactive peptides with regard to regulating a particular biological response of a test cell or tissue.

Figure 1:
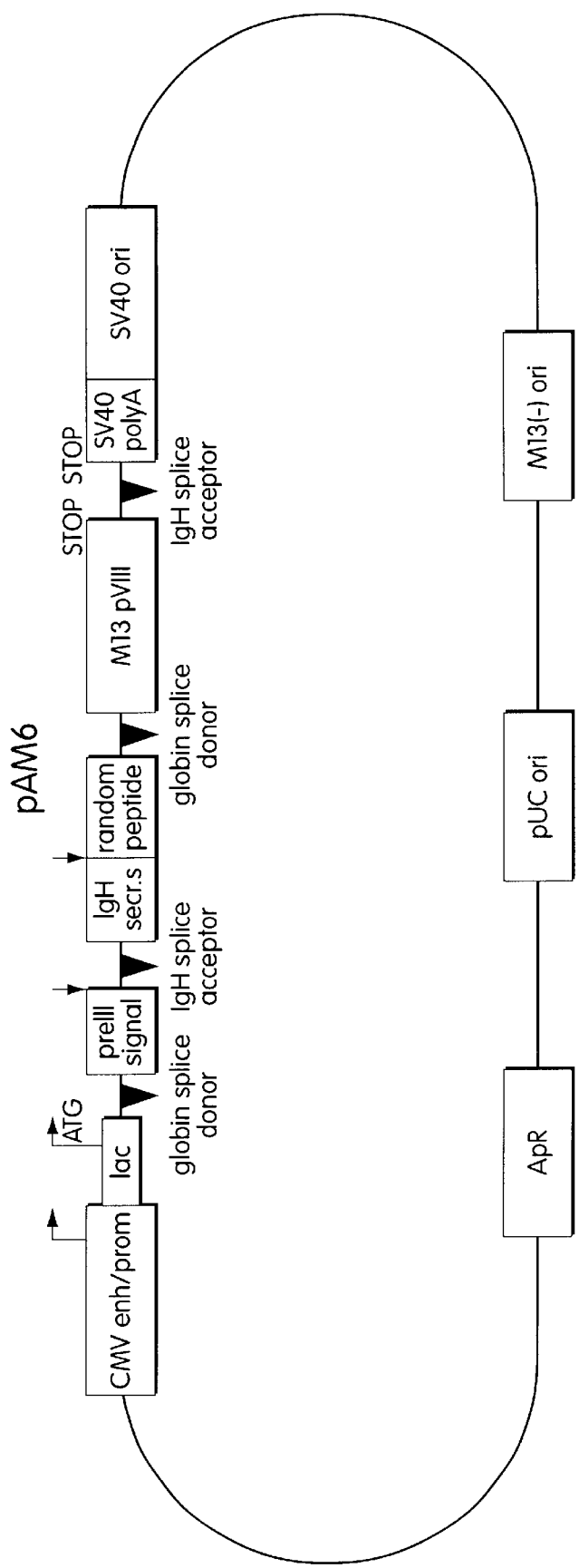
FIG. 1: Schematic of pAM6 M13/COS peptide expression plasmid.
Figure 2:
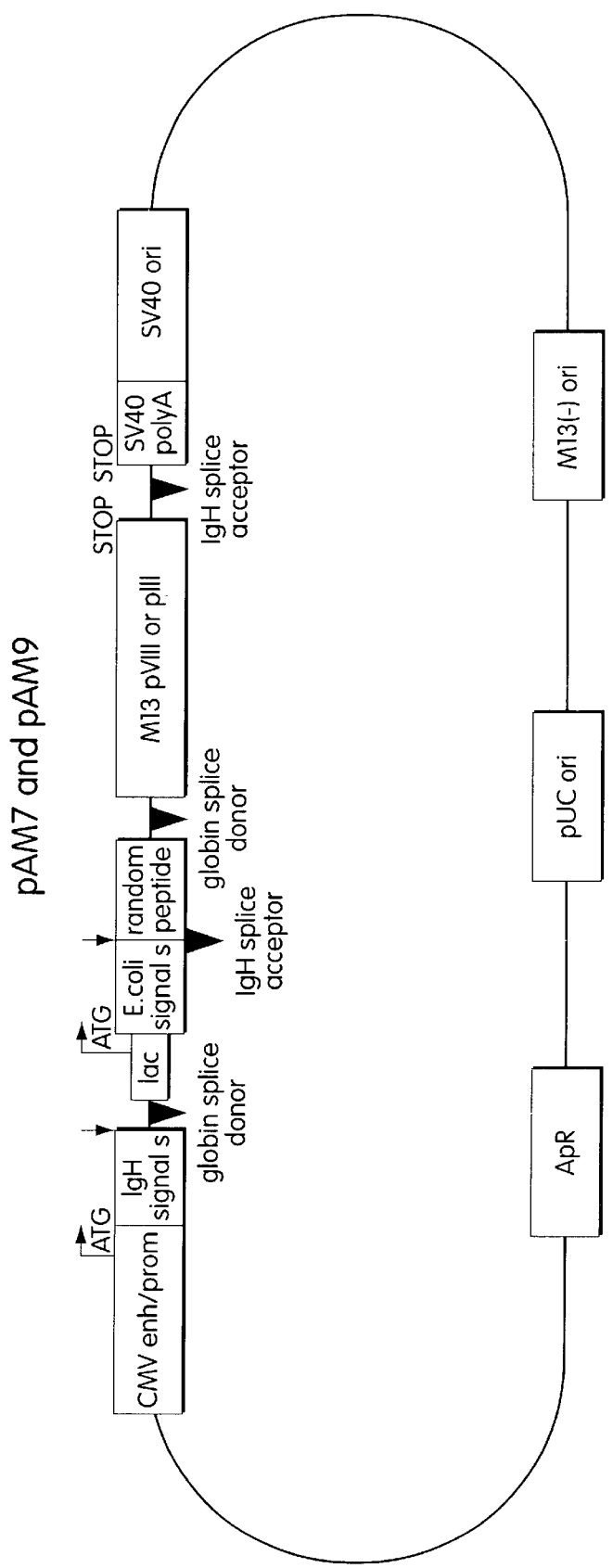
FIG. 2: Schematic of pAM7 & pAM9 M13/COS peptide expression plasmid.
Figure 3:
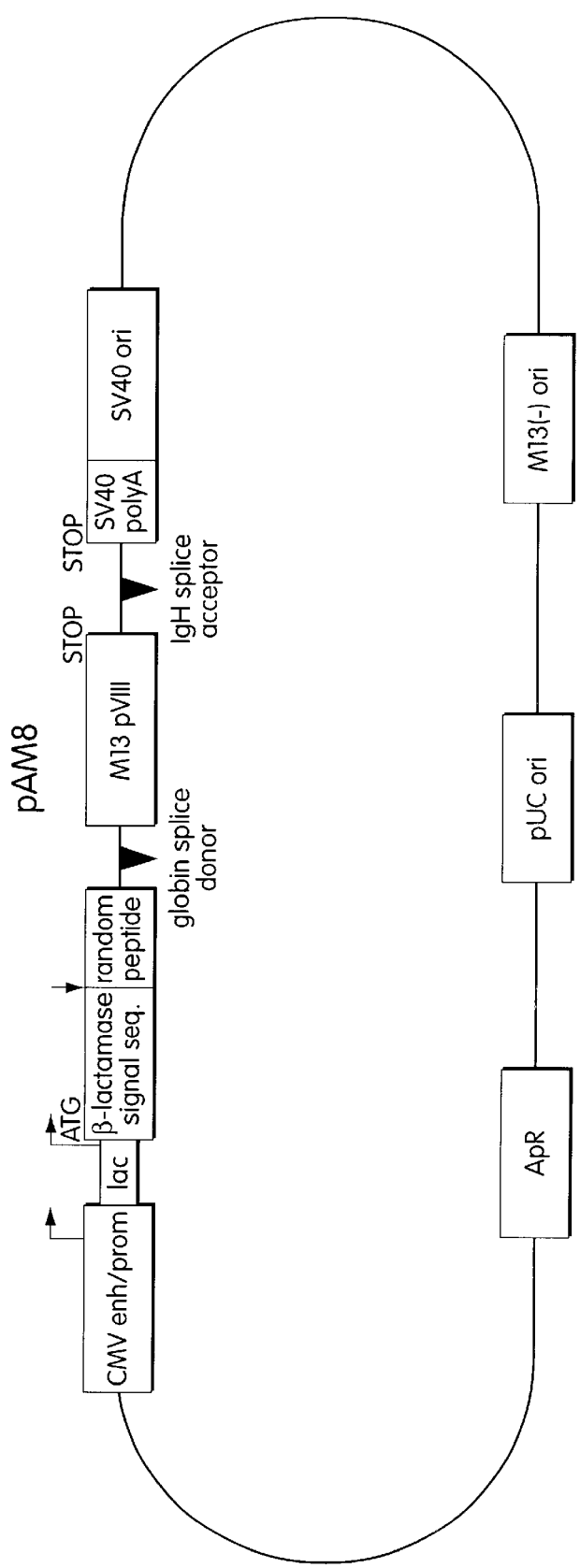
FIG. 3: Schematic of pAM8 M13/COS peptide expression plasmid.

In preferred embodiments, the display mode and secretion mode can be carried out without the need to sub-clone the test peptide coding sequence into another vector. To illustrate, FIGS. 1–3 show exemplary vectors for sequential use in both the display and secretion modes. In bacterial cells, the vectors produce a fusion protein consisting of a secretion signal sequence, the test peptide and the remaining C-terminal portion of the gene VIII protein. The resulting chimeric protein is capable of being incorporated into an M13 phage particle. However, in mammalian cells (such as COS cells), the M13 coding sequences are removed from the mature mRNA by virtue of splice sites which flank the phage sequence. Thus, the mature mRNA, in mammalian cells, encodes a secretion signal sequence and test peptide alone, which is secreted as a soluble peptide from the cell.

One advantage to such embodiments of the subject method is the ability to reduce loss of peptide sequences from the sub-library by eliminating sub-cloning steps.

In an exemplary embodiment, the subject method can be used to identify peptides with anti-anigiogenic activity, e.g., the ability to reversibly inhibit proliferation of endothelial cells. In this regard, the present invention makes available a method for identifiying endothelial inhibitors which can be used to inhibit angiogenesis related diseases and modulating angiogenic processes. As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing. fetal and embryonal development and formation of the corpus luteum, endometrium and placenta. The term "endothelium" means a thin layer of flat epithelial cells that lines serous cavities, lymph vessels, and blood vessels. For instance, peptides isolated by the subject method may be identified by their ability to bind to endothelial cells and overcome the angiogenic activity of endogenous growth factors such as bFGF, in vitro.

II. Definitions

Before further description of the invention, certain terms employed in the specification, examples and appended claims are, for convenience, collected here.

The term "peptide" refers to an oligomer in which the monomers are amino acids (usually alpha-amino acids) joined together through amide bonds. Peptides are two or more amino acid monomers long, but more often are between 5 to 10 amino acid monomers long and can be even longer, i.e. up to 20 amino acids or more, although peptides longer than 20 amino acids are more likely to be called "polypeptides." The term "protein" is well known in the art and usually refers to a very large polypeptide, or set of associated homologous or heterologous polypeptides, that has some biological function. For purposes of the present invention the terms "peptide," "polypeptide," and "protein" are largely interchangeable as all three types can be used to generate the display library and so are collectively referred to as peptides.

The term "simultaneously expressing" refers to the expression of a representative population of a peptide library, e.g., at least 50 percent, more preferably 75, 80, 85, 90, 95 or 98 percent of all the different peptide sequences of a library.

The term "random peptide library" refers to a set of random or semi-random peptides, as well as sets of fusion proteins containing those random peptides (as applicable).

The term "effective amount" refers to an amount sufficient to induce a statistically significant result.

The term "ligand" refers to a molecule that is recognized by a particular protein, e.g., a receptor. Any agent bound by or reacting with a protein is called a "ligand," so the term encompasses the substrate of an enzyme and the reactants of a catalyzed reaction. The term "ligand" does not imply any particular molecular size or other structural or compositional feature other than that the substance in question is capable of binding or otherwise interacting with a protein. A "ligand" may serve either as the natural ligand to which the protein binds or as a functional analogue that may act as an agonist or antagonist.

The language "replicable genetic display package" or "display package" describes a biological particle which has genetic information providing the particle with the ability to replicate. The package can display a fusion protein including a peptide derived from the variegated peptide library. The test peptide portion of the fusion protein is presented by the display package in a context which permits the peptide to bind to a target that is contacted with the display package. The display package will generally be derived from a system that allows the sampling of very large variegated peptide libraries. The display package can be, for example, derived from vegetative bacterial cells, bacterial spores, and bacterial viruses.

The language "differential binding means", as well as "affinity selection" and "affinity enrichment", refer to the separation of members of the peptide display library based on the differing abilities of peptides on the surface of each of the display packages of the library to bind to the target. The differential binding of a target by test peptides of the display can be used in the affinity separation of those peptides which specifically bind the target from those which do not. For example, the affinity selection protocol can also include a pre- or post-enrichment step wherein display packages capable of binding "background targets", e.g., as a negative selection, are removed from the library. Examples of affinity selection means include affinity chromatography, immunoprecipitation, fluorescence activated cell sorting, agglutination, and plaque lifts. As described below, the affinity chromatography includes bio-panning techniques using either purified, immobilized target proteins or the like, as well as whole cells.

The phrases "individually selective manner" and "individually selective binding", with respect to binding of a test peptide with a target protein, refers to the binding of a peptide to a certain protein target which binding is specific for, and dependent on, the molecular identity of the protein target.

The term "solid support" refers to a material having a rigid or semi-rigid surface. Such materials will preferably take the form of small beads, pellets, disks, chips, dishes, multi-well plates, wafers or the like, although other forms may be used. In some embodiments, at least one surface of the substrate will be substantially flat. The term "surface" refers to any generally two-dimensional structure on a solid substrate and may have steps, ridges, kinks, terraces, and the like without ceasing to be a surface.

In an exemplary embodiment of the present invention, the display package is a phage particle which comprises a peptide fusion coat protein that includes the amino acid sequence of a test peptide. Thus, a library of replicable phage vectors, especially phagemids (as defined herein), encoding a library of peptide fusion coat proteins is generated and used to transform suitable host cells. Phage particles formed from the chimeric protein can be separated by affinity selection based on the ability of the peptide associated with a particular phage particle to specifically bind a target. In a preferred embodiment, each individual phage particle of the library includes a copy of the corresponding phagemid encoding the peptide fusion coat protein displayed on the surface of that package. Exemplary phage for generating the present variegated peptide libraries include M13, f1, fd, If1, Ike, Xf, Pf1, Pf3, λ, T4, T7, P2, P4, φX-174, MS2 and f2.

The language "fusion protein" and "chimeric protein" are art-recognized terms which are used interchangeably herein, and include contiguous polypeptides comprising a first polypeptide covalently linked via an amide bond to one or more amino acid sequences which define polypeptide domains that are foreign to and not substantially homologous with any domain of the first polypeptide. One portion of the fusion protein comprises a test peptide, e.g., which can be random or semi-random. A second polypeptide portion of the fusion protein is typically derived from an outer surface protein or display anchor protein which directs the "display package" (as hereafter defined) to associate the test peptide with its outer surface. As described below, where the display package is a phage, this anchor protein can be derived from a surface protein native to the genetic package, such as a viral coat protein. Where the fusion protein comprises a viral coat protein and a test peptide, it will be referred to as a "peptide fusion coat protein". The fusion protein further comprises a signal sequence, which is a short length of amino acid sequence at the amino terminal end of the fusion protein, that directs at least the portion of the fusion protein including the test peptide to be secreted from the cytosol of a cell and localized on the extracellular side of the cell membrane.

Gene constructs encoding fusion proteins are likewise referred to a "chimeric genes" or "fusion genes".

The term "vector" refers to a DNA molecule, capable of replication in a host cell, into which a gene can be inserted to construct a recombinant DNA molecule.

The terms "phage vector" and "phagemid" are art-recognized and generally refer to a vector derived by modification of a phage genome, containing an origin of replication for a bacteriophage, and preferably, though optional, an origin (ori) for a bacterial plasmid. The use of phage vectors rather than the phage genome itself provides greater flexibility to vary the ratio of chimeric peptide/coat protein to wild-type coat protein, as well as supplement the phage genes with additional genes encoding other heterologous polypeptides, such as "auxiliary polypeptides" which may be useful in the "dual" peptide display constructs described below.

The language "helper phage" describes a phage which is used to infect cells containing a defective phage genome or phage vector and which functions to complement the defect. The defect can be one which results from removal or inactivation of phage genomic sequence required for production of phage particles. Examples of helper phage are M13K07.

As used herein, "cell surface receptor" refers to molecules that occur on the surface of cells, interact with the extracellular environment, and (directly or indirectly) transmit or transduce the information regarding the environment intracellularly in a manner that may modulate intracellular second messenger activities or transcription of specific promoters, resulting in transcription of specific genes.

As used herein, "extracellular signals" include a molecule or other change in the extracellular environment that is transduced intracellularly via cell surface proteins that interact, directly or indirectly, with the signal. An extracellular signal or effector molecule includes any compound or substance that in some manner alters the activity of a cell surface protein. Examples of such signals include, but are not limited to, molecules such as acetylcholine, growth factors and hormones, lipids, sugars and nucleotides that bind to cell surface and/or intracellular receptors and ion channels and modulate the activity of such receptors and channels.

As used herein, "extracellular signals" also include as yet unidentified substances that modulate the activity of a cellular receptor, and thereby influence intracellular functions. Such extracellular signals are potential pharmacological agents that may be used to treat specific diseases by modulating the activity of specific cell surface receptors.

"Orphan receptors" is a designation given to a receptors for which no specific natural ligand has been described and/or for which no function has been determined.

As used herein, a "reporter gene construct" is a nucleic acid that includes a "reporter gene" operatively linked to at least one transcriptional regulatory sequence. Transcription of the reporter gene is controlled by these sequences to which they are linked. The activity of at least one or more of these control sequences can be directly or indirectly regulated by the target receptor protein. Exemplary transcriptional control sequences are promoter sequences. A reporter gene is meant to include a promoter-reporter gene construct which is heterologously expressed in a cell.

The term "indicator gene" generically refers to an expressible (e.g., able to be transcribed and [optionally] translated) DNA sequence which is, for example, expressed in response to a signal transduction pathway modulated by a target receptor or ion channel. Exemplary indicator genes include unmodified endogenous genes of the host cell, modified endogenous genes, or a reporter gene of a heterologous construct, e.g., as part of a reporter gene construct.

"Signal transduction" is the processing of physical or chemical signals from the cellular environment through the cell membrane, and may occur through one or more of several mechanisms, such as activation/inactivation of enzymes (such as proteases, or other enzymes which may alter phosphorylation patterns or other post-translational modifications), activation of ion channels or intracellular ion stores, effector enzyme activation via guanine nucleotide binding protein intermediates, formation of inositol phosphate, activation or inactivation of adenylyl cyclase, direct activation (or inhibition) of a transcriptional factor and/or activation.

The term "modulation of a signal transduction activity of a receptor protein" in its various grammatical forms, as used herein, designates induction and/or potentiation, as well as inhibition of one or more signal transduction pathways downstream of a receptor.

Agonists and antagonists are "receptor effector" molecules that modulate signal transduction via a receptor. Receptor effector molecules are capable of binding to the receptor, though not necessarily at the binding site of the natural ligand. Receptor effectors can modulate signal transduction when used alone, i.e. can be surrogate ligands, or can alter signal transduction in the presence ot the natural ligand, either to enhance or inhibit signaling by the natural ligand. For example, "antagonists" are molecules that block or decrease the signal transduction activity of receptor, e.g., they can competitively, noncompetitively, and/or allosterically inhibit signal transduction from the receptor, whereas "agonists" potentiate, induce or otherwise enhance the signal transduction activity of a receptor. The terms "receptor activator" and "surrogate ligand" refer to an agonist which induces signal transduction from a receptor.

The term "compound" as used herein is meant to include both exogenously added test compounds and peptides expressed from a peptide library.

III. Exemplary Embodiments
A. Display Mode

In its "display mode", a library of test peptides is expressed by a population of display packages to form a peptide display library. With respect to the display package on which the variegated peptide library is manifest, it will be appreciated from the discussion provided herein that the display package will preferably be able to be (i) genetically altered to encode heterologous peptide, (ii) maintained and amplified in culture, (iii) manipulated to display the peptide-containing gene product in a manner permitting the peptide to interact with a target during an affinity separation step, and (iv) affinity separated while retaining the nucleotide sequence encoding the test peptide (herein "peptide gene") such that the sequence of the peptide gene can be obtained. In preferred embodiments, the display remains viable after affinity separation.

Ideally, the display package comprises a system that allows the sampling of very large variegated peptide display libraries, rapid sorting after each affinity separation round, and easy isolation of the peptide gene from purified display packages or further manipulation of that sequence in the secretion mode. The most attractive candidates for this type of screening are prokaryotic organisms and viruses, as they can be amplified quickly, they are relatively easy to manipulate, and large number of clones can be created. Preferred display packages include, for example, vegetative bacterial cells, bacterial spores, and most preferably, bacterial viruses (especially DNA viruses). However, the present invention also contemplates the use of eukaryotic cells, including yeast and their spores, as potential display packages.

In addition to commercially available kits for generating phage display libraries (e.g. the Pharmacia *Recombinant Phage Antibody System*, catalog no. 27-9400-01; and the Stratagene SurfZAP™ phage display kit, catalog no. 240612), examples of methods and reagents particularly amenable for use in generating the variegated peptide display library of the present invention can be found in, for example, the Ladner et al. U.S. Pat. No. 5,223,409; the Kang et al. International Publication No. WO 92/18619; the Dower et al. International Publication No. WO 91/17271; the Winter et al. International Publication WO 92/20791; the Markland et al. International Publication No. WO 92/15679; the Breitling et al. International Publication WO 93/01288; the McCafferty et al. International Publication No. WO 92/01047; the Garrard et al. International Publication No. WO 92/09690; the Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) *EMBO J* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982. These systems can, with modifications described herein, be adapted for use in the subject method.

When the display is based on a bacterial cell, or a phage which is assembled periplasmically, the display means of the package will comprise at least two components. The first component is a secretion signal which directs the recombinant peptide to be localized on the extracellular side of the cell membrane (of the host cell when the display package is a phage). This secretion signal can be selected so as to be cleaved off by a signal peptidase to yield a processed, "mature" peptide. The second component is a display anchor protein which directs the display package to associate the test peptide with its outer surface. As described below, this anchor protein can be derived from a surface or coat protein native to the genetic package.

When the display package is a bacterial spore, or a phage whose protein coating is assembled intracellularly, a secretion signal directing the peptide to the inner membrane of the host cell is unnecessary. In these cases, the means for arraying the variegated peptide library comprises a derivative of a spore or phage coat protein amenable for use as a fusion protein.

In some instances it may be necessary to introduce an unstructured polypeptide linker region between portions of the chimeric protein, e.g., between the test peptide and display polypeptide. This linker can facilitate enhanced flexibility of the chimeric protein allowing the test peptide to freely interact with a target by reducing steric hindrance between the two fragments, as well as allowing appropriate folding of each portion to occur. The linker can be of natural origin, such as a sequence determined to exist in random coil between two domains of a protein. Alternatively, the linker can be of synthetic origin. For instance, the sequence (Gly$_4$Ser)$_3$ can be used as a synthetic unstructured linker. Linkers of this type are described in Huston et al. (1988) PNAS 85:4879; and U.S. Pat. Nos. 5,091,513 and 5,258, 498. Naturally occurring unstructured linkers of human origin are preferred as they reduce the risk of immunogenicity.

In the instance wherein the display package is a phage, the cloning site for the test peptide gene sequences in the phagemid should be placed so that it does not substantially interfere with normal phage function. One such locus is the intergenic region as described by Zinder and Boeke, (1982) *Gene* 19:1–10.

The number of possible combinations in a peptide library can get large as the length is increased and selection criteria for degenerating at each position is relaxed. To sample as many combinations as possible depends, in part, on the ability to recover large numbers of transformants. For phage with plasmid-like forms (as filamentous phage), electrotransformation provides an efficiency comparable to that of phage-transfection with in vitro packaging, in addition to a very high capacity for DNA input. This allows large amounts of vector DNA to be used to obtain very large numbers of transformants. The method described by Dower et al. (1988) *Nucleic Acids Res.*, 16:6127–6145, for example, may be used to transform fd-tet derived recombinants at the rate of about $10^7$ transformants/ug of ligated vector into *E. coli* (such as strain MC1061), and libraries may be constructed in fd-tet B1 of up to about 3×10$^8$ members or more. Increasing DNA input and making modifications to the cloning protocol within the ability of the skilled artisan may produce increases of greater than about 10-fold in the recovery of transformants, providing libraries of up to $10^{10}$ or more recombinants.

As will be apparent to those skilled in the art, in embodiments wherein high affinity peptides are sought, an important criteria for the present selection method can be that it is able to discriminate between peptides of different affinity for a particular target, and preferentially enrich for the peptides of highest affinity. Applying the well known principles of peptide affinity and valence (i.e. avidity), it is understood that manipulating the display package to be rendered effectively monovalent can allow affinity enrichment to be carried out for generally higher binding affinities (i.e. binding constants in the range of $10^6$ to $10^{10}$ M$^{-1}$) as compared to the broader range of affinities isolable using a multivalent display package. To generate the monovalent display, the natural (i.e. wild-type) form of the surface or coat protein used to anchor the peptide to the display can be added at a high enough level that it almost entirely eliminates inclusion of the peptide fusion protein in the display package. Thus, a vast majority of the display packages can be generated to include no more than one copy of the peptide fusion protein (see, for example, Garrad et al. (1991) *Bio/Technology* 9:1373–1377). In a preferred embodiment of a monovalent display library, the library of display packages will comprise no more than 5 to 10% polyvalent displays, and more preferably no more than 2% of the display will be polyvalent, and most preferably, no more than 1% polyvalent display packages in the population. The source of the wild-type anchor protein can be, for example, provided by a copy of the wild-type gene present on the same construct as the peptide fusion protein, or provided by a separate construct altogether. However, it will be equally clear that by similar manipulation, polyvalent displays can be generated to isolate a broader range of binding affinities. Such peptides can be useful, for example, in purification protocols where avidity can be desirable.

i) Phages As Display Packages

Bacteriophage are attractive prokaryotic-related organisms for use in the subject method. Bacteriophage are excellent candidates for providing a display system of the variegated peptide library as there is little or no enzymatic activity associated with intact mature phage, and because their genes are inactive outside a bacterial host, rendering the mature phage particles metabolically inert. In general, the phage surface is a relatively simple structure. Phage can be grown easily in large numbers, they are amenable to the practical handling involved in many potential mass screening programs, and they carry genetic information for their own synthesis within a small, simple package. As the peptide gene is inserted into the phage genome, choosing the appropriate phage to be employed in the subject method will generally depend most on whether (i) the genome of the phage allows introduction of the peptide gene either by tolerating additional genetic material or by having replaceable genetic material; (ii) the virion is capable of packaging the genome after accepting the insertion or substitution of genetic material; and (iii) the display of the peptide on the phage surface does not disrupt virion structure sufficiently to interfere with phage propagation.

One concern presented with the use of phage is that the morphogenetic pathway of the phage determines the environment in which the peptide will have opportunity to fold. Periplasmically assembled phage are preferred as the displayed peptides may contain essential disulfides, and such peptides may not fold correctly within a cell. However, in certain embodiments in which the display package forms intracellularly (e.g., where λ phage are used), it has been demonstrated in other instances that disulfide-containing peptides can assume proper folding after the phage is released from the cell.

Another concern related to the use of phage, but also pertinent to the use of bacterial cells and spores as well, is that multiple infections could generate hybrid displays that carry the gene for one particular test peptide yet have two or more different test peptides on their surfaces. Therefore, it can be preferable, though optional, to minimize this possibility by infecting cells with phage under conditions resulting in a low multiple-infection.

For a given bacteriophage, the preferred display means is a protein that is present on the phage surface (e.g. a coat protein). Filamentous phage can be described by a helical lattice; isometric phage, by an icosahedral lattice. Each monomer of each major coat protein sits on a lattice point and makes defined interactions with each of its neighbors. Proteins that fit into the lattice by making some, but not all, of the normal lattice contacts are likely to destabilize the virion by aborting formation of the virion as well as by leaving gaps in the virion so that the nucleic acid is not protected. Thus in bacteriophage, unlike the cases of bacteria and spores, it is generally important to retain in the peptide fusion proteins those residues of the coat protein that interact with other proteins in the virion. For example, when using the M13 cpVIII protein, the entire mature protein will generally be retained with the peptide fragment being added to the N-terminus of cpVIII, while on the other hand it can suffice to retain only the last 100 carboxy terminal residues (or even fewer) of the M13 cpIII coat protein in the peptide fusion protein.

Under the appropriate induction, the test peptide library is expressed and exported, as part of the fusion protein, to the bacterial cytoplasm, such as when the λ phage is employed. The induction of the fusion protein(s) may be delayed until some replication of the phage genome, synthesis of some of the phage structural-proteins, and assembly of some phage particles has occurred. The assembled protein chains then interact with the phage particles via the binding of the anchor protein on the outer surface of the phage particle. The cells are lysed and the phage bearing the library-encoded test peptide (that corresponds to the specific library sequences carried in the DNA of that phage) are released and isolated from the bacterial debris.

To enrich for and isolate phage which encodes a selected test peptide, and thus to ultimately isolate the nucleic acid sequences (the peptide gene) themselves, phage harvested from the bacterial debris are affinity purified. As described below, when a test peptide which specifically binds a particular target is desired, the target can be used to retrieve phage displaying the desired test peptide. The phage so obtained may then be amplified by infecting into host cells. Additional rounds of affinity enrichment followed by amplification may be employed until the desired level of enrichment is reached.

The enriched peptide-phage can also be screened with additional detection-techniques such as expression plaque (or colony) lift (see, e.g., Young and Davis, *Science* (1983) 222:778–782) whereby a labeled target is used as a probe.

a) Filamentous Phage

Filamentous bacteriophages, which include M13, f1, fd, If1, Ike, Xf, Pf1, and Pf3, are a group of related viruses that infect bacteria. They are termed filamentous because they are long, thin particles comprised of an elongated capsule that envelopes the deoxyribonucleic acid (DNA) that forms the bacteriophage genome. The F pili filamentous bacteriophage (Ff phage) infect only gram-negative bacteria by specifically adsorbing to the tip of F pili, and include fd, f1 and M13.

Compared to other bacteriophage, filamentous phage in general are attractive and M13 in particular is especially attractive because: (i) the 3-D structure of the virion is known; (ii) the processing of the coat protein is well understood; (iii) the genome is expandable; (iv) the genome is small; (v) the sequence of the genome is known; (vi) the virion is physically resistant to shear, heat, cold, urea, guanidinium chloride, low pH, and high salt; (vii) the phage is a sequencing vector so that sequencing is especially easy; (viii) antibiotic-resistance genes have been cloned into the genome with predictable results (Hines et al. (1980) *Gene* 11:207–218); (ix) it is easily cultured and stored, with no unusual or expensive media requirements for the infected cells, (x) it has a high burst size, each infected cell yielding 100 to 1000 M13 progeny after infection; and (xi) it is easily harvested and concentrated (Salivar et al. (1964) *Virology* 24: 359–371). The entire life cycle of the filamentous phage M13, a common cloning and sequencing vector, is well understood. The genetic structure of M13 is well known, including the complete sequence (Schaller et al. in *The Single-Stranded DNA Phages* eds. Denhardt et al. (NY: CSHL Press, 1978)), the identity and function of the ten genes, and the order of transcription and location of the promoters, as well as the physical structure of the virion (Smith et al. (1985) *Science* 228:1315–1317; Raschad et al. (1986) *Microbiol Dev* 50:401–427; Kuhn et al. (1987) *Science* 238:1413–1415; Zimmerman et al. (1982) *J Biol Chem* 257:6529–6536; and Banner et al. (1981) *Nature* 289:814–816). Because the genome is small (6423 bp), cassette mutagenesis is practical on RF M13 (Current *Protocols in Molecular Biology*, eds. Ausubel et al. (NY: John Wiley & Sons, 1991)), as is single-stranded oligonucleotide directed mutagenesis (Fritz et al. in *DNA Cloning*, ed by Glover (Oxford, UK: IRC Press, 1985)). M13 is a plasmid and transfomiation system in itself, and an ideal sequencing vector. M13 can be grown on Rec-strains of *E. coli*. The M13 genome is expandable (Messing et al. in *The Single-Stranded DNA Phages*, eds Denhardt et al. (NY: CSHL Press, 1978) pages 449–453; and Fritz et al., supra) and M13 does not lyse cells. Extra genes can be inserted into M13 and will be maintained in the viral genome in a stable manner.

The mature capsule or Ff phage is comprised of a coat of five phage-encoded gene products: cpVIII, the major coat protein product of gene VIII that forms the bulk of the capsule; and four minor coat proteins, cpIII and cpIV at one end of the capsule and cpVII and cpIX at the other end of the capsule. The length of the capsule is formed by 2500 to 3000 copies of cpVIII in an ordered helix array that forms the characteristic filament structure. The gene III-encoded protein (cpIII) is typically present in 4 to 6 copies at one end of the capsule and serves as the receptor for binding of the phage to its bacterial host in the initial phase of infection. For detailed reviews of Ff phage structure, see Rasched et al., *Microbiol. Rev.,* 50:401–427 (1986); and Model et al., in *The Bacteriophages*, Volume 2, R. Calendar, Ed., Plenum Press, pp. 375–456 (1988).

The phage particle assembly involves extrusion of the viral genome through the host cell's membrane. Prior to extrusion, the major coat protein cpVIII and the minor coat protein cpIII are synthesized and transported to the host cell's membrane. Both cpVIII and cpIII are anchored in the host cell membrane prior to their incorporation into the mature particle. In addition, the viral genome is produced and coated with cpV protein. During the extrusion process, cpV-coated genomic DNA is stripped of the cpV coat and simultaneously recoated with the mature coat proteins.

Both cpIII and cpVIII proteins include two domains that provide signals for assembly of the mature phage particle. The first domain is a secretion signal that directs the newly synthesized protein to the host cell membrane. The secretion signal is located at the amino terminus of the polypeptide and targets the polypeptide at least to the cell membrane. The second domain is a membrane anchor domain that provides signals for association with the host cell membrane and for association with the phage particle during assembly. This second signal for both cpvIII and cpII comprises at least a hydrophobic region for spanning the membrane.

The 50 amino acid mature gene VIII coat protein (cpVIII) is synthesized as a 73 amino acid precoat (Ito et al. (979) *PNAS* 76:1199–1203). cpVIII has been extensively studied as a model membrane protein because it can integrate into lipid bilayers such as the cell membrane in an asymmetric orientation with the acidic amino terminus toward the outside and the basic carboxy terminus toward the inside of the membrane. The first 23 amino acids constitute a typical signal-sequence which causes the nascent polypeptide to be inserted into the inner cell membrane. An *E. coli* signal peptidase (SP-I) recognizes amino acids 18, 21, and 23, and, to a lesser extent, residue 22, and cuts between residues 23 and 24 of the precoat (Kuhn et al. (1985) *J. Biol. Chem.* 260:15914–15918; and Kuhn et al. (1 985) *J. Biol. Chem.* 260:15907–15913). After removal of the signal sequence, the amino terminus of the mature coat is located on the periplasmic side of the inner membrane; the carboxy terminus is on the cytoplasmic side. About 3000 copies of the mature coat protein associate side-by-side in the inner membrane.

The sequence of gene VIII is known, and the amino acid sequence can be encoded on a synthetic gene. Mature gene VIII protein makes up the sheath around the circular ssDNA. The gene VIII protein can be a suitable anchor protein because its location and orientation in the virion are known (Banner et al. (1981) *Nature* 289:814–816). Preferably, the peptide is attached to the amino terminus of the mature M13 coat protein to generate the phage display library. As set out above, manipulation of the concentration of both the wild-type cpVIII and Ab/cpVIII fusion in an infected cell can be utilized to decrease the avidity of the display and thereby enhance the detection of high affinity peptides directed to the target(s).

Another vehicle for displaying the peptide is by expressing it as a domain of a chimeric gene containing part or all of gene III, e.g., encoding cpIII. When monovalent displays are required, expressing the peptide as a fusion protein with cpIII can be a preferred embodiment, as manipulation of the ratio of wild-type cpIII to chimeric cpIII during formation of the phage particles can be readily controlled. This gene encodes one of the minor coat proteins of M13. Genes VI, VII, and IX also encode minor coat proteins. Each of these minor proteins is present in about 5 copies per virion and is related to morphogenesis or infection. In contrast, the major coat protein is present in more than 2500 copies per virion. The gene VI, VII, and IX proteins are present at the ends of the virion; these three proteins are not posttranslationally processed (Rasched et al. (1986) *Ann Rev. Microbiol.* 41:507–541). In particular, the single-stranded circular phage DNA associates with about five copies of the gene III protein and is then extruded through the patch of membrane-associated coat protein in such a way that the DNA is encased in a helical sheath of protein (Webster et al. in *The Single-Stranded DNA Phages*, eds Dressler et al. (NY:CSHL Press, 1978).

Manipulation of the sequence of cpIII has demonstrated that the C-terminal 23 amino acid residue stretch of hydrophobic amino acids normally responsible for a membrane anchor function can be altered in a variety of ways and retain the capacity to associate with membranes. Ff phage-based expression vectors were first described in which the cpIII amino acid residue sequence was modified by insertion of polypeptide "targets" (Parmely et al., *Gene* (1988) 73:305–318; and Cwirla et al., *PNAS* (1990) 87:6378–6382) or an amino acid residue sequence defining a single chain peptide domain (McCafferty et al., *Science* (1990) 348:552–554). It has been demonstrated that insertions into gene III can result in the prodution of novel protein domains on the virion outer surface. (Smith (1985) *Science* 228:1315–1317; and de la Cruz et al. (1988) *J. Biol. Chem.* 263:4318–4322). The peptide gene may be fused to gene III at the site used by Smith and by de la Cruz et al., at a codon corresponding to another domain boundary or to a surface loop of the protein, or to the amino terminus of the mature protein.

Generally, the successful cloning strategy utilizing a phage coat protein, such as cpIII of filamentous phage fd, will provide expression of a peptide chain fused to the N-terminus of a coat protein (e.g., cpIII) and transport to the inner membrane of the host where the hydrophobic domain in the C-terminal region of the coat protein anchors the fusion protein in the membrane, with the N-terminus containing the peptide chain protruding into the periplasmic space.

Similar constructions could be made with other filamentous phage. Pf3 is a well known filamentous phage that infects *Pseudomonos aerugenosa* cells that harbor an IncP-I plasmid. The entire genome has been sequenced ((Luiten et al. (1985) *J. Virol.* 56:268–276) and the genetic signals involved in replication and assembly are known (Luiten et al. (1987) DNA 6:129–137). The major coat protein of PF3 is unusual in having no signal peptide to direct its secretion. The sequence has charged residues ASP-7, ARG-37, LYS-40, and PHE44 which is consistent with the amino terminus being exposed. Thus, to cause a peptide to appear on the surface of Pf3, a tripartite gene can be constructed which comprises a signal sequence known to cause secretion in *P. aerugenosa*, fused in-frame to a gene fragment encoding the peptide sequence, which is fused in-frame to DNA encoding the mature Pf3 coat protein. Optionally, DNA encoding a flexible linker of one to 10 amino acids is introduced between the peptide gene fragment and the Pf3 coat-protein gene. This tripartite gene is introduced into Pf3 so that it does not interfere with expression of any Pf3 genes. Once the signal sequence is cleaved off, the peptide is in the periplasm and the mature coat protein acts as an anchor and phage-assembly signal.

b) Bacteriophage φX174

The bacteriophage φX174 is a very small icosahedral virus which has been thoroughly studied by genetics, biochemistry, and electron microscopy (see *The Single Stranded DNA Phages* (eds. Den hardt et al. (NY:CSHL Press, 1978)). Three gene products of φX174 are present on the outside of the mature virion: F (capsid), G (major spike protein, 60 copies per virion), and H (minor spike protein, 12 copies per virion). The G protein comprises 175 amino acids, while H comprises 328 amino acids. The F protein interacts with the single-stranded DNA of the virus. The proteins F, G, and H are translated from a single mRNA in the viral infected cells. As the virus is so tightly constrained because several of its genes overlap, φX174 is not typically used as a cloning vector due to the fact that it can accept very little additional DNA. However, mutations in the viral G gene (encoding the G protein) can be rescued by a copy of the wild-type G gene carried on a plasmid that is expressed in the same host cell (Chambers et al. (1982) *Nuc Acid Res* 10:6465–6473). In one embodiment, one or more stop codons are introduced into the G gene so that no G protein is produced from the viral genome. The variegated peptide gene library can then be fused with the nucleic acid sequence of the H gene. An amount of the viral G gene equal to the size of peptide gene fragment is eliminated from the φX174 genome, such that the size of the genome is ultimately unchanged. Thus, in host cells also transformed with a second plasmid expressing the wild-type G protein, the production of viral particles from the mutant virus is rescued by the exogenous G protein source. Where it is desirable that only one test peptide be displayed per φX174 particle, the second plasmid can further include one or more copies of the wild-type H protein gene so that a mix of H and test peptide/H proteins will be predominated by the wild-type H upon incorporation into phage particles.

c) Large DNA Phage

Phage such as λ or T4 have much larger genomes than do M13 or φX174, and have more complicated 3-D capsid structures than M13 or φPX174, with more coat proteins to choose from. In embodiments of the invention whereby the test peptide library is processed and assembled into a functional form and associates with the bacteriophage particles within the cytoplasm of the host cell, bacteriophage λ and derivatives thereof are examples of suitable vectors. The intracellular morphogenesis of phage λ can potentially prevent protein domains that ordinarily contain disulfide bonds from folding correctly. However, variegated libraries expressing a population of functional peptides, which include such bonds, have been generated in λ phage. (Huse et al. (1989) *Science* 246:1275–1281; Mullinax et al. (1990) *PNAS* 87:8095–8099; and Pearson et al. (1991) *PNAS*

88:2432–2436). Such strategies take advantage of the rapid construction and efficient transformation abilities of λ phage.

When used for expression of peptide sequences (ixogenous nucleotide sequences), may be readily inserted into a λ vector. For instance, variegated peptide libraries can be constructed by modification of λ ZAP II through use of the multiple cloning site of a λ ZAP II vector (Huse et al. supra).

ii) Bacterial Cells as Display Packages

Recombinant peptides are able to cross bacterial membranes after the addition of appropriate secretion signal sequences to the N-terminus of the protein (Better et al (1988) *Science* 240:1041–1043; and Skerra et al. (1988) *Science* 240:1038–1041). In addition, recombinant peptides have been fused to outer membrane proteins for surface presentation. For example, one strategy for displaying peptides on bacterial cells comprises generating a fusion protein by inserting the peptide into cell surface exposed portions of an integral outer membrane protein (Fuchs et al. (1991) *Bio/Technology* 9:1370–1372). In selecting a bacterial cell to serve as the display package, any well-characterized bacterial strain will typically be suitable, provided the bacteria may be grown in culture, engineered to display the test peptide library on its surface, and is compatible with the particular affinity selection process practiced in the subject method. Among bacterial cells, the preferred display systems include *Salmonella typhirnurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and especially *Escherichia coli*. Many bacterial cell surface proteins useful in the present invention have been characterized, and works on the localization of these proteins and the methods of determining their structure include Benz et al. (1988) *Ann Rev Microbiol* 42: 359–393; Balduyck et al. (1985) *Biol Chem Hoppe-Seyler* 366:9–14; Ehrmann et al (1990) *PNAS* 87:7574–7578; Heijne et al. (1990) *Protein Engineering* 4:109–112; Ladner et al. U.S. Pat. No. 5,223,409; Ladner et al. WO88/06630; Fuchs et al. (1991) *Bio/technology* 9:1370–1372; and Goward et al. (1992) *TIBS* 18:136–140.

To further illustrate, the LamB protein of *E coli* is a well understood surface protein that can be used to generate a variegated library of test peptides on the surface of a bacterial cell (see, for example, Ronco et al. (1990) *Biochemie* 72:183–189; van der Weit et al. (1990) *Vaccine* 8:269–277; Charabit et al. (1988) *Gene* 70:181–189; and Ladner U.S. Pat. No. 5,222,409). LamB of *E. coli* is a porin for maltose and maltodextrin transport, and serves as the receptor for adsorption of bacteriophages λ and K10. LamB is transported to the outer membrane if a functional N-terminal signal sequence is present (Benson et al. (1984) *PNAS* 81:3830–3834). As with other cell surface proteins, LamB is synthesized with a typical signal-sequence which is subsequently removed. Thus, the variegated peptide gene library can be cloned into the LamB gene such that the resulting library of fusion proteins comprise a portion of LamB sufficient to anchor the protein to the cell membrane with the test peptide fragment oriented on the extracellular side of the membrane. Secretion of the extracellular portion of the fusion protein can be facilitated by inclusion of the LamB signal sequence, or other suitable signal sequence, as the N-terminus of the protein.

The *E. coli* LamB has also been expressed in functional form in *S. typhimurium* (Harkki et al. (1987) *Mol Gen Genet* 209:607–611), *V. cholerae* (Harkki et al. (1986) *Microb Pathol* 1:283–288), and *K. pneumonia* (Wehmeier et al. (1989) *Mol Gen Genet* 215:529–536), so that one could display a population of test peptides in any of these species as a fusion to *E. coli* LamB. Moreover, *K pneumonia* expresses a maltoporin similar to LamB which could also be used. In *P. aeruginosa*, the D1 protein (a homologue of LamB) can be used (Trias et al. (1988) *Biochem Biophys Acta* 938:493–496). Similarly, other bacterial surface proteins, such as PAL, OmpA, OmpC, OmpF, PhoE, pilin, BtuB, FepA, FhuA, lutA, FecA and FhuE, may be used in place of LamB as a portion of the display means in a bacterial cell.

In another exemplary embodiment, the fusion protein can be derived using the FliTrx™ Random Peptide Display Library (Invitrogen). That library is a diverse population of random dodecapeptides inserted within the thioredoxin active-site loop inside the dispensable region of the bacterial flagellin gene (fliC). The resultant recombinant fusion protein (FLITRX) is exported and assembled into partially functional flagella on the bacterial cell surface, displaying the random peptide library.

Peptides are fused in the middle of thioredoxin, therefore, both their N- and C-termini are anchored by thioredoxin's tertiary structure. This results in the display of a constrained peptide. By contrast, phage display proteins are fused to the N-terminus of phage coat proteins in an unconstrained manner. The unconstrained molecules possess many degrees of conformational freedom which may result in the lack of proper interaction with the target molecule. Without proper interaction, many potential protein-protein interactions may be missed.

Moreover, phage display is limited by the low expression levels of bacteriophage coat proteins. FliTrx™ and similar methods can overcome this limitation by using a strong promoter to drive expression of the test peptide fusions that are displayed as multiple copies.

According to the present invention, it is contemplated that the FliTrx vector can be modified to provide, similar to the illustrated vectors of the attached figures, a vector which is differentially spliced in mammalian cells to yield a secreted, soluble test peptide.

iii) Bacterial Spores as Display Packages

Bacterial spores also have desirable properties as display package candidates in the subject method. For example, spores are much more resistant than vegetative bacterial cells or phage to chemical and physical agents, and hence permit the use of a great variety of affinity selection conditions. Also, Bacillus spores neither actively metabolize nor alter the proteins on their surface. However, spores have the disadvantage that the molecular mechanisms that trigger sporulation are less well worked out than is the formation of M13 or the export of protein to the outer membrane of *E. coli*, though such a limitation is not a serious detractant from their use in the present invention.

Bacteria of the genus Bacillus form endospores that are extremely resistant to damage by heat, radiation, desiccation, and toxic chemicals (reviewed by Losick et al. (1986) *Ann Rev Genet* 20:625–669). This phenomenon is attributed to extensive intermolecular cross-linking of the coat proteins. In certain embodiments of the subject method, such as those which include relatively harsh affinity separation steps, Bacillus spores can be the preferred display package. Endospores from the genus Bacillus are more stable than are, for example, exospores from Streptomyces. Moreover, *Bacillus subtilis* forms spores in 4 to 6 hours, whereas Streptomyces species may require days or weeks to sporulate. In addition, genetic knowledge and manipulation is much more developed for *B. subtilis* than for other spore-forming bacteria.

Viable spores that differ only slightly from wild-type are produced in B. subtilis even if any one of four coat proteins is missing (Donovan et al. (1987) J Mol Biol 196:1–10). Moreover, plasmid DNA is commonly included in spores, and plasmid encoded proteins have been observed on the surface of Bacillus spores (Debro et al. (1986) J Bacteriol 165:258–268). Thus, it can be possible during sporulation to express a gene encoding a chimeric coat protein comprising a peptide of the variegated gene library, without interfering materially with spore formation.

To illustrate, several polypeptide components of B. subtilis spore coat (Donovan et al. (1987) J Mol Biol 196:1–10) have been characterized. The sequences of two complete coat proteins and amino-terminal fragments of two others have been determined. Fusion of the test peptide sequence to cotC or cotD fragments is likely to cause the peptide to appear on the spore surface. The genes of each of these spore coat proteins are preferred as neither cotC or cotD are post-translationally modified (see Ladner et al. U.S. Pat. No. 5,223,409).

iv) Selecting Peptides from the Display Mode

Upon expression, the variegated peptide display is subjected to affinity enrichment in order to select for test peptides which bind preselected targets. The term "affinity separation" or "affinity enrichment" includes, but is not limited to: (1) affinity chromatography utilizing immobilized targets, (2) immunoprecipitation using soluble targets, (3) fluorescence activated cell sorting, (4) agglutination, and (5) plaque lifts. In each embodiment, the library of display packages are ultimately separated based on the ability of the associated test peptide to bind the target of interest. See, for example, the Ladner et al. U.S. Pat. No. 5,223,409; the Kang et al. International Publication No. WO 92/18619; the Dower et al. International Publication No. WO 91/17271; the Winter et al. International Publication WO 92/20791; the Markland et al. International Publication No. WO 92/15679; the Breitling et al. International Publication WO 93/01288; the McCafferty et al. International Publication No. WO 92/01047; the Garrard et al. International Publication No. WO 92/09690; and the Ladner et al. International Publication No. WO 90/02809. In most preferred embodiments, the display library will be pre-enriched for peptides specific for the target by first contacting the display library with any negative controls or other targets for which differential binding by the test peptide is desired. Subsequently, the non-binding fraction from that pre-treatment step is contacted with the target and peptides from the display which are able to specifically bind the target are isolated.

With respect to affinity chromatography, it will be generally understood by those skilled in the art that a great number of chromatography techniques can be adapted for use in the present invention, ranging from column chromatography to batch elution, and including ELISA and biopanning techniques. Typically, where the target is a component of a cell, rather than a whole cell, the target is immobilized on an insoluble carrier, such as sepharose or polyacrylamide beads, or, alternatively, the wells of a microtitre plate. As described below, in instances where no purified source of the target is readily available, such as the case with many cell surface receptors, the cells on which the target is displayed may serve as the insoluble matrix carrier.

The population of display packages is applied to the affinity matrix under conditions compatible with the binding of the test peptide to a target. The population is then fractionated by washing with a solute that does not greatly effect specific binding of peptides to the target, but which substantially disrupts any non-specific binding of the display package to the target or matrix. A certain degree of control can be exerted over the binding characteristics of the peptides recovered from the display library by adjusting the conditions of the binding incubation and subsequent washing. The temperature, pH, ionic strength, divalent cation concentration, and the volume and duration of the washing can select for peptides within a particular range of affinity and specificity. Selection based on slow dissociation rate, which is usually predictive of high affinity, is a very practical route. This may be done either by continued incubation in the presence of a saturating amount of free hapten (if available), or by increasing the volume, number, and length of the washes. In each case, the rebinding of dissociated peptide-display package is prevented, and with increasing time, peptide-display packages of higher and higher affinity are recovered. Moreover, additional modifications of the binding and washing procedures may be applied to find peptides with special characteristics. The affinities of some peptides are dependent on ionic strength or cation concentration. This is a useful characteristic for peptides to be used in affinity purification of various proteins when gentle conditions for removing the protein from the peptide are required. Specific examples are peptides which depend on $Ca^{++}$ for binding activity and which lose or gain binding affinity in the presence of EGTA or other metal chelating agent. Such peptides may be identified in the recombinant peptide library by a double screening technique isolating first those that bind the target in the presence of $Ca^{++}$, and by subsequently identifying those in this group that fail to bind in the presence of EGTA.

After "washing" to remove non-specifically bound display packages, when desired, specifically bound display packages can be eluted by either specific desorption (using excess target) or non-specific desorption (using pH, polarity reducing agents, or chaotropic agents). In preferred embodiments, the elution protocol does not kill the organism used as the display package such that the enriched population of display packages can be further amplified by reproduction. The list of potential eluants includes salts (such as those in which one of the counter ions is $Na^+$, $NH_4^+$, $Rb^+$, $SO_4^{2-}$, $H_2PO_4^-$, citrate, $K^+$, $Li^+$, $Cs^+$, $HSO_4^-$, $CO_3^{2-}$, $Ca^{2+}$, $Sr^{2+}$, $Cl^-$, $PO_4^{2-}$, $HCO_3^-$, $Mg_2^+$, $Ba_2^+$, $Br^-$, $HPO_4^{2-}$, or acetate), acid, heat, and, when available, soluble forms of the target target (or analogs thereof). Because bacteria continue to metabolize during the affinity separation step and are generally more susceptible to damage by harsh conditions, the choice of buffer components (especially eluates) can be more restricted when the display package is a bacteria rather than for phage or spores. Neutral solutes, such as ethanol, acetone, ether, or urea, are examples of other agents useful for eluting the bound display packages.

In preferred embodiments, affinity enriched display packages are iteratively amplified and subjected to further rounds of affinity separation until enrichment of the desired binding activity is detected. In certain embodiments, the specifically bound display packages, especially bacterial cells, need not be eluted per se, but rather, the matrix bound display packages can be used directly to inoculate a suitable growth media for amplification.

Where the display package is a phage particle, the fusion protein generated with the coat protein can interfere substantially with the subsequent amplification of eluted phage particles, particularly in embodiments wherein the cpIII protein is used as the display anchor. Even though present in only one of the 5–6 tail fibers, some peptide constructs because of their size and/or sequence, may cause severe defects in the infectivity of their carrier phage. This causes a loss of phage from the population during reinfection and amplification following each cycle of panning. In one embodiment, the peptide can be derived on the surface of the display package so as to be susceptible to proteolytic cleavage which severs the covalent linkage of at least the target binding sites of the displayed peptide from the remaining package. For instance, where the cpIII coat protein of M13 is employed, such a strategy can be used to obtain infectious phage by treatment with an enzyme which cleaves between the test peptide portion and cpIII portion of a tail fiber fusion protein (e.g. such as the use of an enterokinase cleavage recognition sequence).

To further minimize problems associated with defective infectivity, DNA prepared from the eluted phage can be transformed into host cells by electroporation or well known chemical means. The cells are cultivated for a period of time sufficient for marker expression, and selection is applied as typically done for DNA transformation. The colonies are amplified, and phage harvested for a subsequent round(s) of panning.

After isolation of display packages which encode peptides having a desired binding specificity for the target, the test peptides for each of the purified display packages can be tested for biological activity in the secretion mode of the subject method.

B. Secretion Mode

In the "secretion mode," the combinatorial peptide library, which has been enriched in the display mode, is transfected into and expressed by eukaryotic cells. In this mode, the test peptides are secreted by the host cells and screened for biological activity.

In preferred embodiments, and illustrated in the drawings, the subject vectors are constructed to include eukaryotic splice sites such that, in the mature mRNA, elements required for the display mode in prokaryotic cells are spliced out—at least those elements which would interfere with the secretion mode. A variety of naturally and non-naturally occurring splice sites are available in the art and can be selected for, e.g., optimization in particular eukaryotic cells selected.

In preferred embodiments, the vectors of the subject invention are used to transfect a cell that can be co-cultured with a target cell. A biologically active protein secreted by the cells expressing the combinatorial library will diffuse to neighboring target cells and induce a particular biological response, such as to illustrate, proliferation or differentiation, or activation of a signal transduction pathway which is directly detected by other phenotypic criteria. The pattern of detection of biological activity will resemble a gradient function, and will allow the isolation (generally after several repetitive rounds of selection) of cells producing peptides having certain activity in the assay. Likewise, antagonists of a given factor can be selected in similar fashion by the ability of the cell producing a functional antagonist to protect neighboring cells from the effect of exogenous factor added to the culture media.

To further illustrate, target cells are cultured in 24-well microtitre plates. Other cells are transfected with the combinatorial peptide library, recovered after the display mode step, and cultured in cell culture inserts (e.g. Collaborative Biomedical Products, Catalog #40446) that are able to fit into the wells of the microtitre plate. The cell culture inserts are placed in the wells such that recombinant test peptides secreted by the cells in the insert can diffuse through the porous bottom of the insert and contact the target cells in the microtitre plate wells. After a period of time sufficient for a secreted test peptide to produce a measurable response in the target cells, the inserts are removed and the effect of the peptides on the target cells determined. For example, where the target cell is a neural crest cell and the activity desired from the test peptides is the induction of neuronal differentiation, then fluorescently-labeled antibodies specific for Islet-1 or other neuronal markers can be used to score for induction in the target cells as indicative of a functional neurotrophic peptide in that well. Cells from the inserts corresponding to wells which score positive for activity can be split and re-cultured on several inserts, the process being repeated until the active peptide is identified.

When screening for bioactivity of test peptides, intracellular second messenger generation can be measured directly. For instance, a variety of intracellular effectors have been identified as being receptor- or ion channel-regulated, including adenylyl cyclase, cyclic GMP, phosphodiesterases, phosphoinositidases, phosphoinositol kinases, and phospholipases, as well as a variety of ions.

In one embodiment, the GTPase enzymatic activity by G proteins can be measured in plasma membrane preparations by determining the breakdown of $\gamma^{32}P$ GTP using techniques that are known in the art (For example, see *Signal Transduction: A Practical Approach*. G. Milligan, Ed. Oxford University Press, Oxford England). When receptors that modulate cAMP are tested, it will be possible to use standard techniques for cAMP detection, such as competitive assays which quantitate $[^3H]$cAMP in the presence of unlabelled cAMP.

Certain receptors and ion channels stimulate the activity of phospholipase C which stimulates the breakdown of phosphatidylinositol 4,5, bisphosphate to 1,4,5-IP3 (which mobilizes intracellular Ca++) and diacylglycerol (DAG) (which activates protein kinase C). Inositol lipids can be extracted and analyzed using standard lipid extraction techniques. DAG can also be measured using thin-layer chromatography. Water soluble derivatives of all three inositol lipids (IP1, IP2, IP3) can also be quantitated using radiolabelling techniques or HPLC.

The other product of PIP2 breakdown, DAG can also be produced from phosphatidyl choline. The breakdown of this phospholipid in response to receptor-mediated signaling can also be measured using a variety of radiolabelling techniques.

The activation of phospholipase A2 can easily be quantitated using known techniques, including, for example, the generation of arachadonate in the cell.

In various cells, e.g., mammalian cells, specific proteases are induced or activated in each of several arms of divergent signaling pathways. These may be independently monitored by following their unique activities with substrates specific for each protease.

In the case of certain receptors and ion channels, it may be desirable to screen for changes in cellular phosphorylation. Such assay formats may be useful when, for example, the assay is designed to detect an agonist or antagonist of a receptor kinase or phosphatase. For example, immunoblotting (Lyons and Nelson (1984) *Proc. Natl. Acad. Sci. USA* 81:7426–7430) using anti-phosphotyrosine, anti-phosphoserine or abti-phosphothreonine antibodies. In addition, tests for phosphorylation could be also useful when the receptor itself may not be a kinase, but activates protein kinases or phosphatase that function downstream in the signal transduction pathway.

One such cascade is the MAP kinase pathway that appears to mediate both mitogenic, differentiation and stress responses in different cell types. Stimulation of growth factor receptors results in Ras activation followed by the sequential activation of c-Raf, MEK, and p44 and p42 MAP kinases (ERK1 and ERK2). Activated MAP kinase then phosphorylates many key regulatory proteins, including p90RSK and Elk-1 that are phosphorylated when MAP kinase translocates to the nucleus. Homologous pathways exist in mammalian and yeast cells. For instance, an essential part of the S. cerevisiae pheromone signaling pathway is comprised of a protein kinase cascade composed of the products of the STE11, STE7, and FUS3/KSS1 senes (the latter pair are distinct and functionally redundant). Accordingly, phosphorylation and/or activation of members of this kinase cascade can be detected and used to quantitate receptor engagement. Phosphotyrosine specific antibodies are available to measure increases in tyrosine phosphorylation and phospho-specific antibodies are commercially available (New England Biolabs, Beverly, Mass.).

In yet another embodiment, the signal transduction pathway of interest may upregulate expression or otherwise activate an enzyme which is capable of modifying a substrate which can be added to the cell. The signal can be detected by using a detectable substrate, in which case lose of the substrate signal is monitored, or alternatively, by using a substrate which produces a detectable product. In preferred embodiments, the conversion of the substrate to product by the activated enzyme produces a detectable change in optical characteristics of the test cell, e.g., the substrate and/or product is chromogenically or fluorogenically active. In an illustrative embodiment the signal transduction pathway causes a change in the activity of a proteolytic enzyme, altering the rate at which it cleaves a substrate peptide (or simply activates the enzyme towards the substrate). The peptide includes a fluorogenic donor radical, e.g., a fluorescence emitting radical, and an acceptor radical, e.g., an aromatic radical which absorbs the fluorescence energy of the fluorogenic donor radical when the acceptor radical and the fluorogenic donor radical are covalently held in close proximity. See, for example, U.S. Pat. Nos. 5,527,681, 5,506,115, 5,429,766, 5,424,186, and 5,316,691; and Capobianco et al. (1992) Anal Biochem 204:96–102. For example, the substrate peptide has a fluorescence donor group such as 1-aminobenzoic acid (anthranilic acid or ABZ) or aminomethylcoumarin (AMC) located at one position on the peptide and a fluorescence quencher group, such as lucifer yellow, methyl red or nitrobenzo-2-oxo-1,3-diazole (NBD), at a different position near the distal end of the peptide. A cleavage site for the activated enzyme will be disposed between each of the sites for the donor and acceptor groups. The intramolecular resonance energy transfer from the fluorescence donor molecule to the quencher will quench the fluorescence of the donor molecule when the two are sufficiently proximate in space, e.g., when the peptide is intact. Upon cleavage of the peptide, however, the quencher is separated from the donor group, leaving behind a fluorescent fragment. Thus, activation of the enzyme results in cleavage of the detection peptide, and dequenching of the fluorescent group.

In still other embodiments, the detectable signal can be produced by use of enzymes or chromogenic/fluorscent probes whose activities are dependent on the concentration of a second messanger, e.g., such as calcium, hydrolysis products of inositol phosphate, cAMP, etc. For example , the mobilization of intracellular calcium or the influx of calcium from outside the cell can be measured using standard techniques. The choice of the appropriate calcium indicator, fluorescent, bioluminescent, metallochromic, or Ca++-sensitive microelectrodes depends on the cell type and the magnitude and time constant of the event under study (Borle (1990) Environ Health Perspect 84:45–56). As an exemplary method of Ca++ detection, cells could be loaded with the Ca++ sensitive fluorescent dye fura-2 or indo-1, using standard methods, and any change in Ca++ measured using a fluorometer.

As certain embodiments described above suggest, in addition to directly measuring second messenger production, the signal transduction activity of a receptor or ion channel pathway can be measured by detection of a transcription product, e.g., by detecting receptor/channel-mediated transcriptional activation (or repression) of a gene (s). Detection of the transcription product includes detecting the gene transcript, detecting the product directly (e.g., by immunoassay) or detecting an activity of the protein (e.g., such as an enzymatic activity or chromogenic/fluorogenic activity); each of which is generally referred to herein as a means for detecting expression of the indicator gene. The indicator gene may be an unmodified endogenous gene of the host cell, a modified endogenous gene, or a part of a completely heterologous construct, e.g., as part of a reporter gene construct.

In one embodiment, the indicator gene is an unmodified endogenous gene. For example, the instant method can rely on detecting the transcriptional level of such endogenous genes as the c-fos gene (e.g., in mammalian cells) or the Bar1 or Fus1 genes (e.g., in yeast cells) in response to such signal transduction pathways as originating from G protein coupled receptors.

In certain instances, it may be desirable to increase the level of transcriptional activation of the endogenous indicator gene by the signal pathway in order to, for example, improve the signal-to-noise of the test system, or to adjust the level of response to a level suitable for a particular detection technique. In one embodiment, the transcriptional activation ability of the signal pathway can be amplified by the overexpression of one or more of the proteins involved in the intracellular signal cascade. particularly enzymes involved in the pathway. For example, increased expression of Jun kinases (JNKs) can potentiate the level of transcriptional activation by a signal in an MEKK/JNKK pathway. Likewise, overexpression of one or more signal transduction proteins in the yeast pheromone pathway can increase the level of Fus1 and/or Bar1 expression. This approach can, of course, also be used to potentiate the level of transcription of a heterologous reporter gene as well.

In other embodiments, the sensitivity of an endogenous indicator gene can be enhanced by manipulating the promoter sequence at the natural locus for the indicator gene. Such manipulation may range from point mutations to the endogenous regulatory elements to gross replacement of all or substantial portions of the regulatory elements. In general, manipulation of the genomic sequence for the indicator gene can be carried out using techniques known in the art, including homologous recombination.

In another exemplary embodiment, the promoter (or other transcriptional regulatory sequences) of the endogenous gene can be "switched out" with a heterologous promoter sequence, e.g., to form a chimeric gene at the indicator gene locus. Again, using such techniques as homologous recombination, the regulatory sequence can be so altered at the genomic locus of the indicator gene.

In still another embodiment, a heterologous reporter gene construct can be used to provide the function of an indicator gene. Reporter gene constructs are prepared by operatively linking a reporter gene with at least one transcriptional regulatory element. If only one transcriptional regulatory element is included it must be a regulatable promoter. At least one the selected transcriptional regulatory elements must be indirectly or directly regulated by the activity of the selected cell-surface receptor whereby activity of the receptor can be monitored via transcription of the reporter genes.

Many reporter genes and transcriptional regulatory elements are known to those of skill in the art and others may be identified or synthesized by methods known to those of skill in the art.

Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101), human placental secreted alkaline phosphatase (Cullen and Malim (1992) Methods in Enzymol. 216:362–368); β-lactamase or GST.

Transcriptional control elements for use in the reporter gene constructs, or for modifying the genomic locus of an indicator gene include, but are not limited to, promoters, enhancers, and repressor and activator binding sites. Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477–485), such as c-fos. Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

Other promoters and transcriptional control elements, in addition to those described above, include the vasoactive intestinal peptide (VIP) gene promoter (cAMP responsive; Fink et al. (1988), Proc. Natl. Acad. Sci. 85:6662–6666); the somatostatin gene promoter (cAMP responsive; Montminy et al. (1986), Proc. Natl. Acad. Sci. 8.3:6682–6686); the proenkephalin promoter (responsive to cAMP, nicotinic agonists, and phorbol esters; Comb et al. (1986), Nature 323:353–356); the phosphoenolpyruvate carboxy-kinase gene promoter (cAMP responsive; Short et al. (1986), J. Biol. Chem. 261:9721–9726); the NGFI-A gene promoter (responsive to NGF, cAMP, and serum; Changelian et al. (1989). Proc. Natl. Acad. Sci. 86:377–381); and others that may be known to or prepared by those of skill in the art.

In the case of receptors which modulate cyclic AMP, a transcriptional based readout can be constructed using the cyclic AMP response element binding protein, CREB, which is a transcription factor whose activity is regulated by phosphorylation at a particular serine (S133). When this serine residue is phosphorylated, CREB binds to a recognition sequence known as a CRE (cAMP Responsive Element) found to the 5' of promotors known to be responsive to elevated cAMP levels. Upon binding of phosphorylated CREB to a CRE, transcription from this promoter is increased.

Phosphorylation of CREB is seen in response to both increased cAMP levels and increased intracellular Ca levels. Increased cAMP levels result in activation of PKA, which in turn phosphorylates CREB and leads to binding to CRE and transcriptional activation. Increased intracellular calcium levels results in activation of calcium/calmodulin responsive kinase II (CaM kinase II). Phosphorylation of CREB by CaM kinase II is effectively the same as phosphorylation of CREB by PKA, and results in transcriptional activation of CRE containing promotors.

Therefore, a transcriptionally-based readout can be constructed in cells containing a reporter gene whose expression is driven by a basal promoter containing one or more CRE. Changes in the intracellular concentration of Ca++ (a result of alterations in the activity of the receptor upon engagement with a ligand) will result in changes in the level of expression of the reporter gene if: a) CREB is also co-expressed in the cell, and b) either an endogenous or heterologous CaM kinase phosphorylates CREB in response to increases in calcium or if an exogenously expressed CaM kinase II is present in the same cell. In other words, stimulation of PLC activity may result in phosphorylation of CREB and increased transcription from the CRE-construct, while inhibition of PLC activity may result in decreased transcription from the CRE-responsive construct.

As described in Bonni et al. (1993) Science 262:1575–1579, the observation that CNTF treatment of SK-N-MC cells leads to the enhanced interaction of STAT/p91 and STAT related proteins with specific DNA sequences suggested that these proteins might be key regulators of changes in gene expression that are triggered by CNTF. Consistent with this possibility is the finding that DNA sequence elements similar to the consensus DNA sequence required for STAT/p91 binding are present upstream of a number of genes previously found to be induced by CNTF (e.g., Human c-fos, Mouse c-fos, Mouse tis11, Rat junB, Rat SOD-1, and CNTF). Those authors demonstrated the ability of STAT/p91 binding sites to confer CNTF responsiveness to a non-responsive reporter gene. Accordingly, a reporter construct for use in the present invention for detecting signal transduction through STAT proteins, such as from cytokine receptors, can be generated by using −71 to +109 of the mouse c-fos gene fused to the bacterial chloramphenicol acetyltransferase gene (−71fosCAT) or other detectable marker gene. Induction by a cytokine receptor induces the tyrosine phosphorylation of STAT and STAT-related proteins, with subsequent translocation and binding of these proteins to the STAT-RE. This then leads to activation of transcription of genes containing this DNA element within their promoters.

In preferred embodiments, the reporter gene is a gene whose expression causes a phenotypic change which is screenable or selectable. If the change is selectable, the phenotypic change creates a difference in the growth or survival rate between cells which express the reporter gene and those which do not. If the change is screenable, the phenotype change creates a difference in some detectable characteristic of the cells, by which the cells which express the marker may be distinguished from those which do not. Selection is preferable to screening in that it can provide a means for amplifying from the cell culture those cells which express a test polypeptide which is a receptor effector.

The marker gene is coupled to the receptor signaling pathway so that expression of the marker gene is dependent on activation of the receptor. This coupling may be achieved by operably linking the marker gene to a receptor-responsive promoter. The term "receptor-responsive promoter" indicates a promoter which is regulated by some product of the target receptor's signal transduction pathway.

Alternatively, the promoter may be one which is repressed by the receptor pathway, thereby preventing expression of a product which is deleterious to the cell. With a receptor repressed promoter, one screens for agonists by linking the promoter to a deleterious gene, and for antagonists, by linking it to a beneficial gene. Repression may be achieved by operably linking a receptor-induced promoter to a gene encoding mRNA which is antisense to at least a portion of the mRNA encoded by the marker gene (whether in the coding or flanking regions), so as to inhibit translation of that mRNA. Repression may also be obtained by linking a receptor-induced promoter to a gene encoding a DNA binding repressor protein, and incorporating a suitable operator site into the promoter or other suitable region of the marker gene.

The marker gene may also be a screenable gene. The screened characteristic may be a change in cell morphology, metabolism or other screenable features. Suitable markers include β-galactosidase (Xgal, $C_{12}$FDG, Salmon-gal, Magenta-Gal (latter two from Biosynth Ag)), alkaline phosphatase, horseradish peroxidase, exo-glucanase (product of yeast exb1 gene; nonessential, secreted); luciferase; bacterial green fluorescent protein; (human placental) secreted alkaline phosphatase (SEAP); and chloramphenicol transferase (CAT). Some of the above can be engineered so that they are secreted (although not β-galactosidase). A preferred screenable marker gene is beta-galactosidase; yeast cells expressing the enzyme convert the colorless substrate Xgal into a blue pigment. Again, the promoter may be receptor-induced or receptor-inhibited.

In certain assays it may be desirable to use changes in growth in the screening procedure. For example, one of the consequences of activation of the pheromone signal pathway in wild-type yeast is growth arrest. If one is testing for an antagonist of a G protein-coupled receptor, such as a human receptor engineered into a yeast cell, this normal response of growth arrest can be used to select cells in which the pheromone response pathway is inhibited. That is, cells exposed to a test compound will be growth arrested if the compound is an agonist, but will grow normally if the compound is neutral or an antagonist. Thus, the growth arrest response can be used to advantage to discover compounds that function as agonists or antagonists. Moreover, the effect of growth arrest can provide a selective advantage in the presence of an agent which is cytotoxic to mitotic cells. For example, during the growth arrest window, the cytotoxic agent is added to the culture. Cells which proceed through the cell-cycle, e.g., which are not growth arrested, will be killed. At some time after the addition of the cytotoxic agent, it can be washed from the culture, and surviving cells permited to proceed with proliferation. Cells which were arrested by the test compound will be enriched in the surviving population.

However, in certain embodiments the growth arrest consequent to activation of the pheromone response pathway is an undesirable effect since cells that bind agonists stop growing while surrounding cells that fail to bind peptides will continue to grow. The cells of interest, then, will be overgrown or their detection obscured by the background cells, confounding identification of agonistic peptides. To overcome this problem the present invention teaches engineering the cell such that: 1) growth arrest does not occur as a result of exogenous signal pathway activation (e.g., by inactivating the FAR1 gene); and/or 2) a selective growth advantage is conferred by activating the pathway (e.g., by transforming an auxotrophic mutant with a HIS3 gene under the control of a pheromone-responsive promoter, and applying selective conditions).

It is, of course, desirable that the exogenous receptor be exposed on a continuing basis to the peptides. Unfortunately, this is likely to result in desensitization of the pheromone pathway to the stimulus. For example, the mating signal transduction pahtway is known to become desensitized by several mechanisms including pheromone degradation and modification of the function of the receptor, G proteins,s and/or downstream elements of the pheromone signal transduction by the products of the SST2, STE50, AFR1 (Konopka, J. B. (1993) *Mol. Cell. Biol.* 13:6876–6888) and SGV1, MSG5, and SIG1 genes. Selected mutations in these genes can lead to hypersensitivity to pheromone and an inability to adapt to the presence of pheromone. For example, introduction of mutations that interfere with function into strains expressing heterologous G protein-coupled receptors constitutes a significant improvement on wild type strains and enables the development of extremely sensitive bioassays for compounds that interact with the receptors. Other mutations e.g. STE50, sgv1,bar1, ste2,ste3,pik1, msg5, sig1, and aft1, have the similar effect of increasing the sensitivity of the bioassay. Thus desensitization may be avoided by mutating (which may include deleting) the SST2 gene so that it no longer produces a functional protein, or by mutating one of the other genes listed above.

If the endogenous homolog of the receptor is produced by the yeast cell, the assay will not be able to distinguish between peptides which interact with the endogenous receptor and those which interact with the exogenous receptor. It is therefore desirable that the endogenous gene be deleted or otherwise rendered nonfunctional.

Suitable host cells for generating the target cells of subject assay include prokaryotes, yeast, or higher eukaryotic cells, including plant and animal cells, especially mammalian cells. Prokaryotes include gram negative or gram positive organisms. Examples of suitable mammalian host cell lines include the COS-7 line of monkey kidney cells (ATCC CRL 1651) (Gluzman (1981) Cell 23:175) CV-1 cells (ATCC CCL 70), L cells, C127, 3T3, Chinese hamster ovary (CHO), HeLa, HEK-293, SWISS 3T3, and BHK cell lines.

If yeast cells are used, the yeast may be of any species which are cultivable and in which an exogenous receptor can be made to engage the appropriate signal transduction machinery of the host cell. Suitable species include *Kluyverei lactis, Schizosaccharomyces pombe*, and *Ustilaqo maydis, Saccharomyces cerevisiae* is preferred. Other yeast which can be used in practicing the present invention are *Neurospora crassa, Aspergillus niger, Aspergillus nidulans, Pichia pastoris, Candida tropicalis*, and *Hansenula polymorpha*. The term "yeast", as used herein, includes not only yeast in a strictly taxonomic sense, i.e., unicellular organisms, but also yeast-like multicellular fungi or filamentous fungi.

The choice of appropriate host cell will also be influenced by the choice of detection signal. For instance, reporter constructs, as described below, can provide a selectable or screenable trait upon transcriptional activation (or inactivation) in response to a signal transduction pathway coupled to the target receptor. The reporter gene may be an unmodified gene already in the host cell pathway. It may be a host cell gene that has been operably linked to a "receptor-responsive" promoter. Alternatively, it may be a heterologous gene (e.g., a "reporter gene construct") that has been so linked. Suitable genes and promoters are discussed below. In other embodiments, second messenger generation can be measured directly in the detection step, such as mobilization of intracellular calcium or phospholipid metabolism are quantitated. In yet other embodiments indicator genes can be used to detect receptor-mediated signaling.

Accordingly, it will be understood that to achieve selection or screening, the host cell must have an appropriate phenotype. For example, generating a pheromone-responsive chimeric HIS3 gene in a yeast that has a wild-type HIS3 gene would frustrate genetic selection. Thus, to achieve nutritional selection, an auxotrophic strain is wanted.

A variety of complementations for use in the subject assay can be constructed. Indeed, many yeast genetic complementation with mammalian signal transduction proteins have been described in the art. For example, Mosteller et al. (1994) Mol Cell Biol 14:1104–12 demonstrates that human Ras proteins can complement loss of ras mutations in *S. cerevisiae*. Moreover, Toda et al. (1986) Princess Takamatsu Symp 17: 253–60 have shown that human ras proteins can complement the loss of RAS1 and RAS2 proteins in yeast, and hence are functionally homologous. Both human and yeast RAS proteins can stimulate the magnesium and guanine nucleotide-dependent adenylate cyclase activity present in yeast membranes. Ballester et al. (1989) Cell 59: 681–6 describe a vector to express the mammalian GAP protein in the yeast *S. cerevisiae*. When expressed in yeast, GAP inhibits the function of the human ras protein, and complements the loss of IRA1. IRA1 is a yeast gene that encodes a protein with homology to GAP and acts upstream of RAS. Mammalian GAP can therefore function in yeast and interact with yeast RAS. Wei et al. (1994) *Gene* 151: 279–84 describes that a human Ras-specific guanine nucleotide-exchange factor, Cdc25GEF, can complement the loss of CDC25 function in *S. cerevisiae*. Martegani et al. (1992) EMBO J 11: 2151–7 describe the cloning by functional complementation of a mouse cDNA encoding a homolog of CDC25, a *Saccharomyces cerevisiae* RAS activator. Vojtek et al. (1993) J Cell Sci 105: 777–85 and Matviw et al. (1992) Mol Cell Biol 12: 5033–40 describe how a mouse CAP protein, e.g., an adenylyl cyclase associated protein associated with ras-mediated signal transduction, can complements defects in *S. cerevisiae*. Papasavvas et al. (1992) Biochem Biophys Res Commun 184:1378–85 also suggest that inactivated yeast adenyl cyclase can be complemented by a mammalian adenyl cyclase gene. Hughes et al. (1993) Nature 364: 349–52 describe the complementation of byr1 in fission yeast by mammalian MAP kinase kinase (MEK). Parissenti et al. (1993) Mol Cell Endocrinol 98: 9–16 describes the reconstitution of bovine protein kinase C (PKC) in yeast. The Ca(2+)- and phospholipid-dependent Ser/Thr kinase PKC plays important roles in the transduction of cellular signals in mammalian cells. Marcus et al. (1995) PNAS 92: 6180–4 suggests the complementation of shk1 null mutations in *S. pombe* by the either the structurally related *S. cerevisiae* Ste20 or mammalian p65PAK protein kinases.

"Inactivation", with respect to genes of the host cell, means that production of a functional gene product is prevented or inhibited. Inactivation may be achieved by deletion of the gene, mutation of the promoter so that expression does not occur, or mutation of the coding sequence so that the gene product is inactive. Inactivation may be partial or total.

"Complementation", with respect to genes of the host cell, means that at least partial function of inactivated gene of the host cell is supplied by an exogenous nucleic acid. For instance, yeast cells can be "mammalianized", and even "humanized", by complementation of receptor and signal transduction proteins with mammalian homologs. To illustrate, inactivation of a yeast Byr2/Ste11 gene can be complemented by expression of a human MEKK gene.

C. Generations of Peptide Libraries

The variegated peptide libraries of the subject method can be generated by any of a number of methods, and, though not limited by, preferably exploit recent trends in the preparation of chemical libraries. For instance, chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential test sequences. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

As used herein, "variegated" refers to the fact that a population of peptides is characterized by having a peptide sequence which differ from one member of the library to the next. For example, in a given peptide library of n amino acids in length, the total number of different peptide sequences in the library is given by the product of $\{v_1 \times v_2 \times \ldots v_{n-1} \times v_n\}$ where each $v_n$ represents the number different amino acid residues occurring at position n of the peptide. In a preferred embodiment of the present invention, the peptide display collectively produces a peptide library including at least 96 to $10^7$ different peptides, so that diverse peptides may be simultaneously assayed for the ability to interact with the target protein.

In one embodiment, the test peptide library is derived to express a combinatorial library of peptides which are not based on any known sequence, nor derived from cDNA. That is, the sequences of the library are largely, if not entirely, random. It will be evident that the peptides of the library may range in size from dipeptides to large proteins.

In another embodiment, the peptide library is derived to express a combinatorial library of peptides which are based at least in part on a known polypeptide sequence or a portion thereof (though preferably not a cDNA library). That is, the sequences of the library is semi-random, being derived by combinatorial mutagenesis of a known sequence(s). See, for example, Ladner et al. PCT publication WO 90/02909; Garrard et al., PCT publication WO 92/09690; Marks et al. (1992) *J. Biol. Chem.* 267:16007–16010; Griffths et al. (1993) *EMBO J* 12:725–734; Clackson et al. (1991) *Nature* 352:624–628; and Barbas et al. (1992) *PNAS* 89:4457–4461. Accordingly, polypeptide(s) which are known ligands for a target protein can be mutagenized by standard techniques to derive a variegated library of polypeptide sequences which can further be screened for agonists and/or antagonists. The purpose of screening such combinatorial peptide libraries is to generate, for example, homologs of known polypeptides which can act as either agonists or antagonists, or alternatively, possess novel activities all together. To illustrate, a ligand can be engineered by the present method to provide more efficient binding or specificity to a cognate receptor, yet still retain at least a portion of an activity associated with wild-type ligand. Thus, combinatorially-derived homologs can be generated to have an increased potency relative to a naturally occurring form of the protein. Likewise, homologs can be generated by the present approach to act as antagonists, in that they are able to mimic, for example, binding to the target, yet not induce any biological response, thereby inhibiting the action of authentic ligand.

In preferred embodiments, the combinatorial polypeptides are in the range of 3–100 amino acids in length, more preferably at least 5–50, and even more preferably at least 10, 13, 15, 20 or 25 amino acid residues in length. Preferably, the polypeptides of the library are of uniform length. It will be understood that the length of the combinatorial peptide does not reflect any extraneous sequences which may be present in order to facilitate expression, e.g., such as signal sequences or invariant portions of a fusion protein.

In preferred embodiments, the test peptide is flanked by cysteine residues in order to provide a constrained environment. For example, the test peptide may be represented in the general formula Cys-$(Xaa)_{3-23}$-Cys.

The harnessing of biological systems for the generation of peptide diversity is now a well established technique which can be exploited to generate the peptide libraries of the subject method. The source of diversity is the combinatorial chemical synthesis of mixtures of oligonucleotides. Oligonucleotide synthesis is a well-characterized chemistry that allows tight control of the composition of the mixtures created. Degenerate DNA sequences produced are subsequently placed into an appropriate genetic context for expression as peptides.

There are two principal ways in which to prepare the required degenerate mixture. In one method, the DNAs are synthesized a base at a time. When variation is desired at a base position dictated by the genetic code a suitable mixture of nucleotides is reacted with the nascent DNA, rather than the pure nucleotide reagent of conventional polynucleotide synthesis. The second method provides more exact control over the amino acid variation. First, trinucleotide reagents are prepared, each trinucleotide being a codon of one (and only one) of the amino acids to be featured in the peptide library. When a particular variable residue is to be synthesized, a mixture is made of the appropriate trinucleotides and reacted with the nascent DNA. Once the necessary "degenerate" DNA is complete, it must be joined with the DNA sequences necessary to assure the expression of the peptide, as discussed in more detail below, and the complete DNA construct must be introduced into the cell.

Whatever the method may be for generating diversity at the codon level, chemical synthesis of a degenerate gene sequence can be carried out in an automatic DNA synthesizer, and the synthetic genes can then be ligated into an appropriate gene for expression. The purpose of a degenerate set of genes is to provide, in one mixture, all of the sequences encoding the desired set of potential test peptide sequences. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

IV. Exemplary Uses

Because of the flexibility of the system, the subject method can be used in a broad range of applications, including for the selection of peptides having effects on proliferation, differentiation, cell death, cell migration, etc. In preferred embodiments, the target used in the display mode is an extracellular component of a cell. However, it will be appreciated that the target for subject method can be an intracellular component and, during the secretion mode, the system can be augmented with agents which promote the cellular uptake of the test peptides.

In an illustrative embodiment, the subject method is utilized to identify peptides which have antiproliferative activity with respect to one or more types of cells. For instance, in the display mode, the peptide library can be panned with the target cells for which an antiproliferative is desired in order to enrich for peptides which bind to that cell. At that stage, the peptide library can also be panned against one or more control cell lines in order to remove peptides which bind the control cells. In this manner, the peptide library which is then tested in the secretion mode can be enriched for peptides which selectively bind target cell (relative to the control cells). Thus, for example, the display mode can produce a peptide library enriched for peptides which preferentially bind tumor cells relative to normal cells, which preferentially bind p53– cells relative to p53+ cells, which preferentially bind hair follicle cells relative to other epithelial cells, or any other differential binding characteristic.

In the secretion mode, the peptides are tested for antiproliferative activity against the target cell using any of a number of techniques known in the art. For instance, BrdU or other nucleotide uptake can be measured as an indicator of proliferation. As above, the secretion mode can include negative controls in order to select for peptides with specific antiproliferative activity.

In similar fashion, peptides can be isolated from the library based on their ability to induce apoptosis or cell lysis, e.g., in a cell selective manner.

Figure 6:
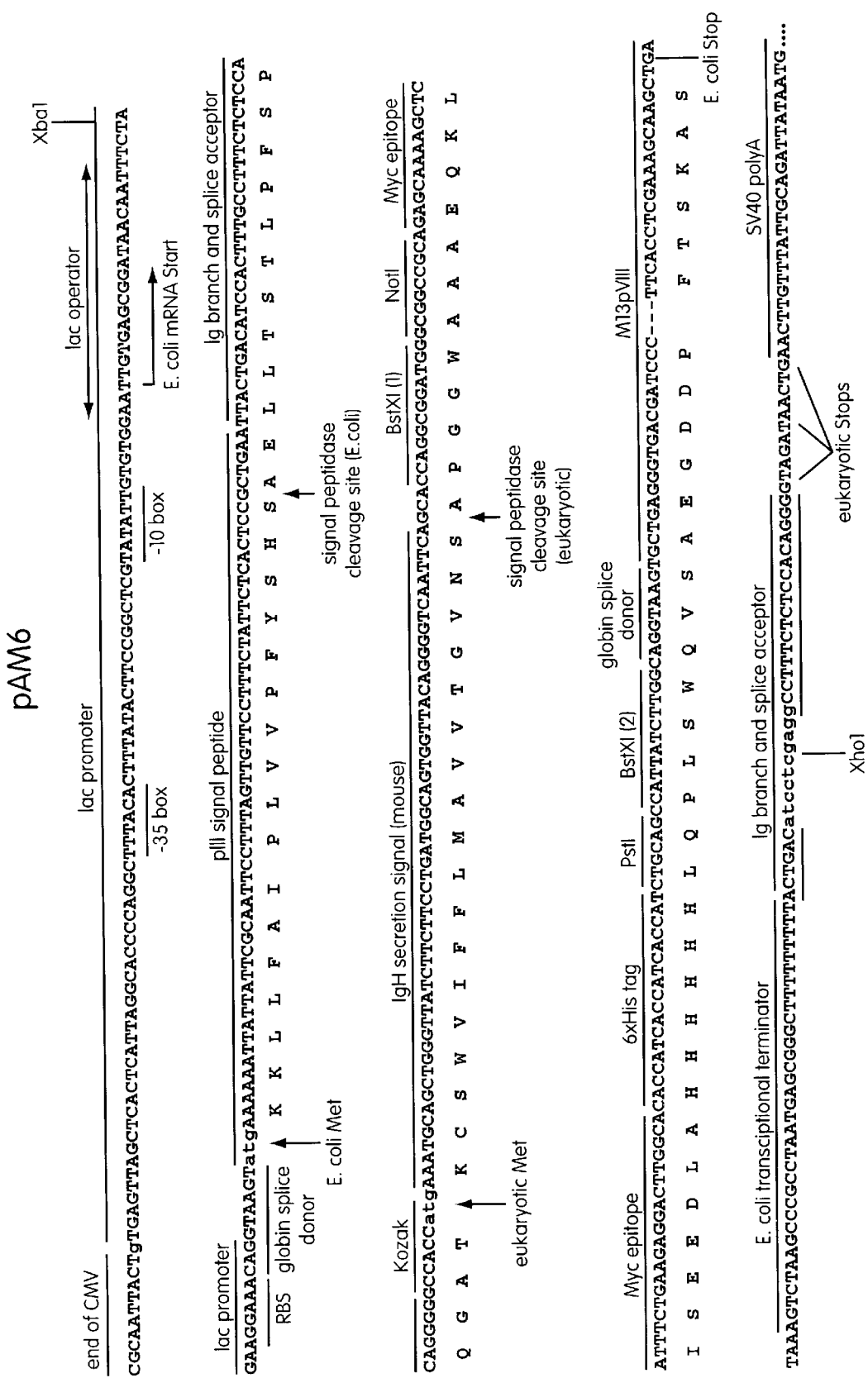
FIG. 6: Nucleotide level depiction of pAM6 M13/COS peptide expression plasmid.

In yet another embodiment, the subject method can be used to identify peptides with angiogenic or antiangiogenic activity. For instance, as illustrated in FIG. 6, the peptide library can be enriched for peptides that bind to endothelial cells but which do not bind to fibroblasts. The resulting sub-library can be screened for peptides which inhibit capillary endothelial cell proliferation and/or endothelial cell migration. Peptides scoring positive for one or both of these activities can also be tested for activity against other cell types, such as smooth muscle cells or fibroblasts, in order to select peptides active only against endothelial cells.

In still another embodiment, the subject method can be used to identify anti-infective peptides, e.g., which are active as anti-fungal or antibacterial agents.

In one embodiment, the assay of the present invention can be used for identifying effectors of a receptor protein or complex thereof. In general, the assay is characterized by the use of a test cell which includes a target receptor or ion channel protein whose signal transduction activity can be modulated by interaction with an extracellular signal, the transduction activity being able to generate a detectable signal.

In general, such embodiments of the subject assay are characterized by the use of a mixture of cells expressing a target receptor protein or ion channel capable of transducing a detectable signal in the reagent cell. The receptor/channel protein can be either endogenous or heterologous. In combination with the disclosed detection means, a culture of the instant reagent cells will provide means for detecting agonists or antagonists of receptor function.

The ability of particular peptides to modulate a signal transduction activity of the target receptor or channel can be scored for by detecting up or down-regulation of the detection signal. For example, second messenger generation (e.g. GTPase activity, phospholipid hydrolysis, or protein phosphorylation patterns as examples) can be measured directly. Alternatively, the use of an indicator gene can provide a convenient readout. In other embodiments a detection means consists of an indicator gene. In any event, a statistically significant change in the detection signal can be used to facilitate identification of compounds which modulate receptor or ion channel activities.

By this method, peptides which induce a signal pathway from a particular receptor or channel can be identified. If a test peptide does not appear to induce the activity of the receptor/channel protein, the assay may be repeated as described above, and modified by the introduction of a step in which the reagent cell is first contacted with a known activator of the target receptor/channel to induce signal transduction, and the test peptide can be assayed for its ability to inhibit the activated receptor/channel, e.g., to identify antagonists. In yet other embodiments, peptides can be screened for those which potentiate the response to a known activator of the receptor.

With respect to the receptor or ion channel, it may be endogenously expressed by the host cell, or it may be expressed from a heterologous gene that has been introduced into the cell. Methods for introducing heterologous DNA into eukaryotic cells are of course well known in the art and any such method may be used. In addition, DNA encoding various receptor proteins is known to those of skill in the art or it may be cloned by any method known to those of skill in the art. In certain embodiments, such as when an exogenous receptor is expressed, it may be desirable to inactivate, such as by deletion, a homologous receptor present in the cell.

In particular, the assays can be used to test functional ligand-receptor or ligand-ion channel interactions for cell surface-localized receptors and channels. As described in more detail below, the subject assay can be used to identify effectors of, for example, G protein-coupled receptors, receptor tyrosine kinases, cytokine receptors, and ion channels. In certain embodiments the method described herein is used for identifying ligands for "orphan receptors" for which no ligand is known.

In preferred embodiments, the receptor is a cell surface receptor, such as: a receptor tyrosine kinase, e.g., an EPH receptor; an ion channel; a cytokine receptor; an multisubunit immune recognition receptor, a chemokine receptor; a growth factor receptor, or a G-protein coupled receptor, such as a chemoattracttractant peptide receptor, a neuropeptide receptor, a light receptor, a neurotransmitter receptor, or a polypeptide hormone receptor.

Preferred G protein coupled receptors include α1A-adrenergic receptor, α1B-adrenergic receptor, α2-adrenergic receptor, α2B-adrenergic receptor, β1-adrenergic receptor, β2-adrenergic receptor, β3-adrenergic receptor, m1 acetylcholine receptor (AChR), m2 AChR, m3 AChR. m4 AChR, m5 AChR, D1 dopamine receptor, D2 dopamine receptor, D3 dopamine receptor, D4 dopamine receptor, D5 dopamine receptor, A1 adenosine receptor, A2b adenosine receptor, 5-HT1a receptor, 5-HT1b receptor, 5HT1-like receptor, 5-HT1d receptor, 5HT1d-like receptor, 5HT1d beta receptor, substance K (neurokinin A) receptor, fMLP receptor, fMLP-like receptor, angiotensin II type 1 receptor, endothelin ETA receptor, endothelin ETB receptor, thrombin receptor, growth hormone-releasing hormone (GHRH) receptor, vasoactive intestinal peptide receptor, oxytocin receptor, somatostatin SSTR1 and SSTR2, SSTR3, cannabinoid receptor, follicle stimulating hormone (FSH) receptor, leutropin (LH/HCG) receptor, thyroid stimulating hormone (TSH) receptor, thromboxane A2 receptor, platelet-activating factor (PAF) receptor, C5a anaphylatoxin receptor, Interleukin 8 (IL-8) IL-8RA, IL-8RB, Delta Opioid receptor, Kappa Opioid receptor, mip-1/RANTES receptor, Rhodopsin, Red opsin, Green opsin, Blue opsin, metabotropic glutamate mGluR1-6, histamine H2 receptor, ATP receptor, neuropeptide Y receptor, amyloid protein precursor receptor, insulin-like growth factor II receptor, bradykinin receptor, gonadotropin-releasing hormone receptor, cholecystokinin receptor, melanocyte stimulating hormone receptor receptor, antidiuretic hormone receptor, glucagon receptor, and adrenocorticotropic hormone II receptor.

Preferred EPH receptors inlcude eph, elk, eck, sek, mek4, hek, hek2, eek, erk, tyro1, tyro4, tyro5, tyro6, tyro11, cek4, cek5, cek6, cek7, cek8, cek9, cek10, bsk, rtk1, rtk2, rtk3, myk1, myk2, ehk1, ehk2, pagliaccio, htk, erk and nuk receptors.

A. Cytokine Receptors

In one embodiment the target receptor is a cytokine receptor. Cytokines are a family of soluble mediators of cell-to-cell communication that includes interleukins, interferons, and colony-stimulating factors. The characteristic features of cytokines lie in their functional redundancy and pleiotropy. Most of the cytokine receptors that constitute distinct superfamilies do not possess intrinsic protein tyrosine kinase domains, yet receptor stimulation usually invokes rapid tyrosine phosphorylation of intracellular proteins, including the receptors themselves. Many members of the cytokine receptor superfamily acitvate the Jak protein tyrosine kinase family, with resultant phosphorylation of the STAT transcriptional activator factors. IL-2, IL-7, IL-2 and Interferon γ have all been shown to activate Jak kinases (Frank et al (1995) *Proc Natl Acad Sci USA* 92:7779–7783); Scharfe et al. (1995) *Blood* 86:2077–2085); (Bacon et al. (1995) *Proc Natl Acad Sci USA* 92:7307–7311); and (Sakatsume et al (1995) *J. Biol Chem* 270:17528–17534). Events downstream of Jak phosphorylation have also been elucidated. For example, exposure of T lymphocytes to IL-2 has been shown to lead to the phosphorylation of signal transducers and activators of transcription (STAT) proteins STAT1α, STAT2β, and STAT3, as well as of two STAT-related proteins, p94 and p95. The STAT proteins were found to translocate to the nucleus and to bind to a specific DNA sequence, thus suggesting a mechanism by which IL-2 may activate speicfic genes involved in immune cell function (Frank et al. supra). Jak3 is associated with the gamma chain of the IL-2, IL-4, and IL-7 cytokine receptors (Fujii et al. (1995) *Proc Natl Acad Sci* 92:5482–5486) and (Musso et al (1995) J Exp Med. 181:1425–1431). The Jak kinases have also been shown to be activated by numerous ligands that signal via cytokine receptors such as, growth hormone and erythropoietin and IL-6 (Kishimoto (1 994) Stem cells Suppl 12:37–44).

Detection means which may be scored for in the present assay, in addition to direct detection of second messengers, such as by changes in phosphorylation, includes reporter constructs or indicator genes which include transcriptional regulatory elements responsive to the STAT proteins. Described infra.

B Multisubunit Immune Recognition Receptor (MIRR).

In another embodiment the receptor is a multisubunit receptor. Receptors can be comprised of multiple proteins referred to as subunits, one category of which is referred to as a multisubunit receptor is a multisubunit immune recognition receptor (MIRR). MIRRs include receptors having multiple noncovalently associated subunits and are capable of interacting with src-family tyrosine kinases. MIRRs can include, but are not limited to, B cell antigen receptors, T cell antigen receptors, Fc receptors and CD22. One example of an MIRR is an antigen receptor on the surface of a B cell. To further illustrate, the MIRR on the surface of a B cell comprises membrane-bound immunoglobulin (mIg) associated with the subunits Ig-α and Ig-β or Ig-γ, which forms a complex capable of regulating B cell function when bound by antigen. An antigen receptor can be functionally linked to an amplifier molecule in a manner such that the amplifier molecule is capable of regulating gene transcription.

Src-family tyrosine kinases are enzymes capable of phosphorylating tyrosine residues of a target molecule. Typically, a src-family tyrosine kinase contains one or more binding domains and a kinase domain. A binding domain of a src-family tyrosine kinase is capable of binding to a target molecule and a kinase domain is capable of phosphorylating a target molecule bound to the kinase. Members of the src family of tyrosine kinases are characterized by an N-terminal unique region followed by three regions that contain different degrees of homology among all the members of the family. These three regions are referred to as src homology region 1 (SH1), src homology region 2 (SH2) and src homology region 3 (SH3). Both the SH2 and SH3 domains are believed to have protein association functions important for the formation of signal transduction complexes. The amino acid sequence of an N-terminal unique region, varies between each src-family tyrosine kinase. An N-terminal unique region can be at least about the first 40 amino acid residues of the N-terminal of a src-family tyrosine kinase.

Syk-family kinases are enzymes capable of phosphorylating tyrosine residues of a target molecule. Typically, a syk-family kinase contains one or more binding domains and a kinase domain. A binding domain of a syk-family tyrosine kinase is capable of binding to a target molecule and a kinase domain is capable of phosphorylating a target molecule bound to the kinase. Members of the syk-family of tyrosine kinases are characterized by two SH2 domains for protein association function and a tyrosine kinase domain.

A primary target molecule is capable of further extending a signal transduction pathway by modifying a second messenger molecule. Primary target molecules can include, but are not limited to, phosphatidylinositol 3-kinase (PI-3K), P21$^{ras}$GAPase-activating protein and associated P190 and P62 protein, phospholipases such as PLCγ1 and PLCγ2, MAP kinase, Shc and VAV. A primary target molecule is capable of producing second messenger molecule which is capable of further amplifying a transduced signal. Second messenger molecules include, but are not limited to diacylglycerol and inositol 1,4,5-triphosphate (IP3). Second messenger molecules are capable of initiating physiological events which can lead to alterations in gene transcription. For example, production of IP3 can result in release of intracellular calcium, which can then lead to activation of calmodulin kinase II, which can then lead to serine phosphorylation of a DNA binding protein referred to as ets-1 proto-onco-protein. Diacylglycerol is capable of activating the signal transduction protein, protein kinase C which affects the activity of the AP1 DNA binding protein complex. Signal transduction pathways can lead to transcriptional activation of genes such as c-fos, egr-1, and c-myc.

Shc can be thought of as an adaptor molecule. An adaptor molecule comprises a protein that enables two other proteins to form a complex (e.g., a three molecule complex). Shc protein enables a complex to form which includes Grb2 and SOS. Shc comprises an SH2 domain that is capable of associating with the SH2 domain of Grb2.

Molecules of a signal transduction pathway can associate with one another using recognition sequences. Recognition sequences enable specific binding between two molecules. Recognition sequences can vary depending upon the structure of the molecules that are associating with one another. A molecule can have one or more recognition sequences, and as such can associate with one or more different molecules.

Signal transduction pathways for MIRR complexes are capable of regulating the biological functions of a cell. Such functions can include, but are not limited to the ability of a cell to grow, to differentiate and to secrete cellular products. MIRR-induced signal transduction pathways can regulate the biological functions of specific types of cells involved in particular responses by an animal, such as immune responses, inflammatory responses and allergic responses. Cells involved in an immune response can include, for example, B cells, T cells, macrophages, dendritic cells, natural killer cells and plasma cells. Cells involved in inflammatory responses can include, for example, basophils, mast cells, eosinophils, neutrophils and macrophages. Cells involved in allergic responses can include, for example mast cells, basophils, B cells, T cells and macrophages.

In exemplary embodiments of the subject assay, the detection signal is a second messengers, such as a phosphorylated src-like protein, includes reporter constructs or indicator genes which include transcriptional regulatory elements such as serum response element (SRE), 12-O-tetradecanoyl-phorbol-13-acetate response element, cyclic AMP response element, c-fos promoter, or a CREB-responsive element.

C. Receptor Tyrosine Kinases

In still another embodiment, the target receptor is a receptor tyrosine kinase. The receptor tyrosine kinases can be divided into five subgroups on the basis of structural similarities in their extracellular domains and the organization of the tyrosine kinase catalytic region in their cytoplasmic domains. Sub-groups I (epidermal growth factor (EGF) receptor-like), II (insulin receptor-like) and the eph/eck family contain cysteine-rich sequences (Hirai et al., (1987) *Science* 238:1717–1720 and Lindberg and Hunter, (1990) *Mol. Cell. Biol.* 10:6316–6324). The functional domains of the kinase region of these three classes of receptor tyrosine kinases are encoded as a contiguous sequence (Hanks et al. (1988) *Science* 241:42–52). Subgroups III (platelet-derived growth factor (PDGF) receptor-like) and IV (the fibro-blast growth factor (FGF) receptors) are characterized as having immunoglobulin (Ig)-like folds in their extracellular domains, as well as having their kinase domains divided in two parts by a variable stretch of unrelated amino acids (Yanden and Ullrich (1988) supra and Hanks et al. (1988) supra).

The family with by far the largest number of known members is the EPH family. Since the description of the prototype, the EPH receptor (Hirai et al. (1987) *Science* 238:1717–1720), sequences have been reported for at least ten members of this family, not counting apparently orthologous receptors found in more than one species. Additional partial sequences, and the rate at which new members are still being reported, suggest the family is even larger (Maisonpierre et al. (1993) *Oncogene* 8:3277–3288; Andres et al. (1994) *Oncogene* 9:1461–1467; Henkemeyer et al. (1994) *Oncogene* 9:1001–1014; Ruiz et al. (1994) *Mech Dev* 46:87–100; Xu et al. (1994) *Development* 120:287–299; Zhou et al. (1994) *J Neurosci Res* 37:129–143; and references in Tuzi and Gullick (1994) *Br J Cancer* 69:417–421). Remarkably, despite the large number of members in the EPH family, all of these molecules were identified as orphan receptors without known ligands.

The expression patterns determined for some of the EPH family receptors have implied important roles for these molecules in early vertebrate development. In particular, the timing and pattern of expression of sek, mek4 and some of the other receptors during the phase of gastrulation and early organogenesis has suggested functions for these receptors in the important cellular interactions involved in patterning the embryo at this stage (Gilardi-Hebenstreit et al. (1992) *Oncogene* 7:2499–2506; Nieto et al. (1992) *Development* 116:1137–1150; Henkemeyer et al., supra; Ruiz et al., supra; and Xu et al., supra). Sek, for example, shows a notable early expression in the two areas of the mouse embryo that show obvious segmentation, namely the somites in the mesoderm and the rhombomeres of the hindbrain; hence the name sek, for segmentally expressed kinase (Gilardi-Hebenstreit et al., supra; Nieto et al., supra). As in Drosophila, these segmental structures of the mammalian embryo are implicated as important elements in establishing the body plan. The observation that Sek expression precedes the appearance of morphological segmentation suggests a role for sek in forming these segmental structures, or in determining segment-specific cell properties such as lineage compartmentation (Nieto et al., supra). Moreover, EPH receptors have been implicated, by their pattern of expression, in the development and maintenance of nearly every tissue in the embryonic and adult body. For instance, EPH receptors have been detected throughout the nervous system, the testes, the cartilaginous model of the skeleton, tooth primordia, the infundibular component of the pituitary, various epithelia tissues, lung, pancreas, liver and kidney tissues. Observations such as this have been indicative of important and unique roles for EPH family kinases in development and physiology, but further progress in understanding their action has been severely limited by the lack of information on their ligands.

As used herein, the terms "EPH receptor" or "EPH-type receptor" refer to a class of receptor tyrosine kinases, comprising at least eleven paralogous genes, though many more orthologs exist within this class, e.g. homologs from different species. EPH receptors, in general, are a discrete group of receptors related by homology and easily reconizable, e.g., they are typically characterized by an extracellular domain containing a characteristic spacing of cysteine residues near the N-terminus and two fibronectin type III repeats (Hirai et al. (1987) *Science* 238:1717–1720; Lindberg et al. (1990) *Mol Cell Biol* 10:6316–6324; Chan et al. (1991) *Oncogene* 6:1057–1061; Maisonpierre et al. (1993) *Oncogene* 8:3277–3288; Andres et al. (1994) *Oncogene* 9:1461–1467; Henkemeyer et al. (1994) *Oncogene* 9:1001–1014; Ruiz et al. (1994) *Mech Dev* 46:87–100; Xu et al. (1 994) *Development* 120:287–299; Zhou et al. (1994) *J Neurosci Res* 37:129–143; and references in Tuzi and Gullick (1994) *Br J Cancer* 69:417–421). Exemplary EPH receptors-include the eph, elk, eck, sek, mek4, hek, hek2, eek, erk, tyro1, tyro4, tyro5, tyro6, tyro11, cek4, cek5, cek6, cek7, cek8, cek9, cek10, bsk, rtk1, rtk2, rtk3, myk1, myk2, ehk1, ehk2, pagliaccio, htk, erk and nuk receptors. The term "EPH receptor" refers to the membrane form of the receptor protein, as well as soluble extracellular fragments which retain the ability to bind the ligand of the present invention.

In exemplary embodiments, the detection signal is provided by detecting phosphorylation of intracellular proteins, e.g., MEKKs, MEKs, or Map kinases, or by the use of reporter constructs or indicator genes which include transcriptional regulatory elements responsive to c-fos and/or c-jun. Described infra.

D. G Protein-Coupled Receptors

One family of signal transduction cascades found in eukaryotic cells utilizes heterotrimeric "G proteins." Many different G proteins are known to interact with receptors. G protein signaling systems include three components: the receptor itself, a GTP-binding protein (G protein), and an intracellular target protein.

The cell membrane acts as a switchboard. Messages arriving through different receptors can produce a single effect if the receptors act on the same type of G protein. On the other hand, signals activating a single receptor can produce more than one effect if the receptor acts on different kinds of G proteins, or if the G proteins can act on different effectors.

In their resting state, the G proteins, which consist of alpha ($\alpha$), beta ($\beta$) and gamma ($\gamma$) subunits, are complexed with the nucleotide guanosine diphosphate (GDP) and are in contact with receptors. When a hormone or other first messenger binds to receptor, the receptor changes conformation and this alters its interaction with the G protein. This spurs the a subunit to release GDP, and the more abundant nucleotide guanosine triphosphate (GTP), replaces it, activating the G protein. The G protein then dissociates to separate the a subunit from the still complexed beta and gamma subunits. Either the $G\alpha$ subunit, or the $G\beta\gamma$ complex, depending on the pathway, interacts with an effector. The effector (which is often an enzyme) in turn converts an inactive precursor molecule into an active "second messenger," which may diffuse through the cytoplasm, triggering a metabolic cascade. After a few seconds, the $G\alpha$ converts the GTP to GDP, thereby inactivating itself. The inactivated $G\alpha$ may then reassociate with the $G\beta\gamma$ complex.

Hundreds, if not thousands, of receptors convey messages through heterotrimeric G proteins, of which at least 17 distinct forms have been isolated. Although the greatest variability has been seen in the a subunit, several different $\beta$ and $\gamma$ structures have been reported. There are, additionally, several different G protein-dependent effectors.

Most G protein-coupled receptors are comprised of a single protein chain that is threaded through the plasma membrane seven times. Such receptors are often referred to as seven-transmembrane receptors (STRs). More than a hundred different STRs have been found, including many distinct receptors that bind the same ligand, and there are likely many more STRs awaiting discovery.

In addition, STRs have been identified for which the natural ligands are unknown; these receptors are termed "orphan" G protein-coupled receptors, as described above. Examples include receptors cloned by Neote et al. (1993) *Cell* 72, 415; Kouba et al. *FEBS Lett.* (1993) 321, 173; Birkenbach et al. (1993) *J. Virol.* 67, 2209.

The "exogenous receptors" of the present invention may be any G protein-coupled receptor which is exogenous to the cell which is to be genetically engineered for the purpose of the present invention. This receptor may be a plant or animal cell receptor. Screening for binding to plant cell receptors may be useful in the development of, e.g., herbicides. In the case of an animal receptor, it may be of invertebrate or vertebrate origin. If an invertebrate receptor, an insect receptor is preferred, and would facilitate development of insecticides. The receptor may also be a vertebrate, more preferably a mammalian, still more preferably a human, receptor. The exogenous receptor is also preferably a seven transmembrane segment receptor.

Known ligands for G protein coupled receptors include: purines and nucleotides, such as adenosine, cAMP, ATP, UTP, ADP, melatonin and the like; biogenic amines (and related natural ligands), such as 5-hydroxytryptamine, acetylcholine, dopamine, adrenaline, adrenaline, adrenaline., histamine, noradrenaline, noradrenaline, noradrenaline., tyramine/octopamine and other related compounds; peptides such as adrenocorticotrophic hormone (acth), melanocyte stimulating hormone (msh), melanocortins, neurotensin (nt), bombesin and related peptides, endothelins, cholecystokinin, gastrin, neurokinin b (nk3), invertebrate tachykinin-like peptides, substance k (nk2), substance p (nk1), neuropeptide y (npy), thyrotropin releasing-factor (trf), bradykinin, angiotensin ii, beta-endorphin, c5a anaphalatoxin, calcitonin, chemokines (also called intercrines), corticotrophic releasing factor (crf), dynorphin, endorphin, fmlp and other formylated peptides, follitropin (fsh), fungal mating pheremones, galanin, gastric inhibitory polypeptide receptor (gip), glucagon-like peptides (glps), glucagon, gonadotropin releasing hormone (gnrh), growth hormone releasing hormone(ghrh), insect diuretic hormone, interleukin-8, leutropin (lh/hcg), metenkephalin, opioid peptides, oxytocin, parathyroid hormone (pth) and pthrp, pituitary adenylyl cyclase activiating peptide (pacap), secretin, somatostatin, thrombin, thyrotropin (tsh), vasoactive intestinal peptide (vip), vasopressin, vasotocin; eicosanoids such as ip-prostacyclin, pg-prostaglandins, tx-thromboxanes; retinal based compounds such as vertebrate 11-cis retinal, invertebrate 11-cis retinal and other related compounds; lipids and lipid-based compounds such as cannabinoids, anandamide, lysophosphatidic acid, platelet activating factor, leukotrienes and the like; excitatory amino acids and ions such as calcium ions and glutamate.

Suitable examples of G-protein coupled receptors include, but are not limited to, dopaminergic, muscarinic cholinergic, a-adrenergic, b-adrenergic, opioid (including delta and mu), cannabinoid, serotoninergic, and GABAergic receptors. Preferred receptors include the 5HT family of receptors, dopamine receptors,C5a receptor and FPRL-1 receptor, cyclo-histidyl-proline-diketoplperazine receptors, melanocyte stimulating hormone release inhibiting factor receptor, and receptors for neurotensin, thyrotropin releasing hormone, calcitonin, cholecytokinin-A, neurokinin-2, histamine-3, cannabinoid, melanocortin, or adrenomodulin, neuropeptide-Y1 or galanin. Other suitable receptors are listed in the art. The term "receptor," as used herein, encompasses both naturally occurring and mutant receptors.

Many of these G protein-coupled receptors, like the yeast a- and α-factor receptors, contain seven hydrophobic amino acid-rich regions which are assumed to lie within the plasma membrane. Specific human G protein-coupled STRs for which genes have been isolated and for which expression vectors could be constructed include those listed herein and others known in the art. Thus, the gene would be operably linked to a promoter functional in the cell to be engineered and to a signal sequence that also functions in the cell. For example in the case of yeast, suitable promoters include Ste2, Ste3 and gal10. Suitable signal sequences include those of Ste2, Ste3 and of other genes which encode proteins secreted by yeast cells. Preferably, when a yeast cell is used, the codons of the gene would be optimized for expression in yeast. See Hoekema et al., (1987) *Mol. Cell Biol.,* 7:2914–24; Sharp, et al., (1986) 14:5125–43.

The homology of STRs is discussed in Dohlman et al., *Ann. Rev. Biochem.,* (1991) 60:653–88. When STRs are compared, a distinct spatial pattern of homology is discernible. The transmembrane domains are often the most similar, whereas the N- and C-terminal regions, and the cytoplasmic loop connecting transmembrane segments V and VI are more divergent.

The functional significance of different STR regions has been studied by introducing point mutations (both substitutions and deletions) and by constructing chimeras of different but related STRs. Synthetic peptides corresponding to individual segments have also been tested for activity. Affinity labeling has been used to identify ligand binding sites.

It is conceivable that when the host cell is a yeast cell, a foreign receptor will fail to functionally integrate into the yeast membrane, and there interact with the endogenous yeast G protein. More likely, either the receptor will need to be modified (e.g., by replacing its V-VI loop with that of the yeast STE2 or STE3 receptor), or a compatible G protein should be provided.

If the wild-type exogenous G protein-coupled receptor cannot be made functional in yeast, it may be mutated for this purpose. A comparison would be made of the amino acid sequences of the exogenous receptor and of the yeast receptors, and regions of high and low homology identified. Trial mutations would then be made to distinguish regions involved in ligand or G protein binding, from those necessary for functional integration in the membrane. The exogenous receptor would then be mutated in the latter region to more closely resemble the yeast receptor, until functional integration was achieved. If this were insufficient to achieve functionality, mutations would next be made in the regions involved in G protein binding. Mutations would be made in regions involved in ligand binding only as a last resort, and then an effort would be made to preserve ligand binding by making conservative substitutions whenever possible.

Preferably, the yeast genome is modified so that it is unable to produce the yeast receptors which are homologous to the exogenous receptors in functional form. Otherwise, a positive assay score might reflect the ability of a peptide to activate the endogenous G protein-coupled receptor, and not the receptor of interest.

(i). Chemoattractant Receptors

The N-formyl peptide receptor is a classic example of a calcium mobilizing G protein-coupled receptor expressed by neutrophils and other phagocytic cells of the mammalian immune system (Snyderman et al. (1988) In *Inflammation: Basic Principles and Clinical Correlates,* pp. 309–323). N-formyl peptides of bacterial origin bind to the receptor and engage a complex activation program that results in directed cell movement, release of inflammatory granule contents, and activation of a latent NADPH oxidase which is important for the production of metabolites of molecular oxygen. This pathway initiated by receptor-ligand interaction is critical in host protection from pyogenic infections. Similar signal transduction occurs in response to the inflammatory peptides C5a and IL-8.

Two other formyl peptide receptor like (FPRL) genes have been cloned based on their ability to hybridize to a fragment of the NFPR cDNA coding sequence. These have been named FPRL1 (Murphy et al. (1992) *J. Biol Chem.* 267:7637–7643) and FPRL2 (Ye et al. (1992) *Biochem Biophys Res. Comm.* 184:582–589). FPRL2 was found to mediate calcium mobilization in mouse fibroblasts transfected with the gene and exposed to formyl peptide. In contrast, although FPRL1 was found to be 69% identical in amino acid sequence to NFPR, it did not bind prototype N-formyl peptides ligands when expressed in heterologous cell types. This lead to the hypothesis of the existence of an as yet unidentified ligand for the FPRL1 orphan receptor (Murphy et al. supra).

(ii.) G Proteins

In the case of an exogenous G-protein coupled receptor, the yeast cell must be able to produce a G protein which is activated by the exogenous receptor, and which can in turn activate the yeast effector(s). The art suggests that the endogenous yeast G$\alpha$ subunit (e.g., GPA) will be often be sufficiently homologous to the "cognate" G$\alpha$ subunit which is natively associated with the exogenous receptor for coupling to occur. More likely, it will be necessary to genetically engineer the yeast cell to produce a foreign G$\alpha$ subunit which can properly interact with the exogenous receptor. For example, the G$\alpha$ subunit of the yeast G protein may be replaced by the G$\alpha$ subunit natively associated with the exogenous receptor.

Dietzel and Kurjan, (1987) *Cell*, 50:1001) demonstrated that rat G$\alpha$s functionally coupled to the yeast G$\alpha\gamma$ complex. However, rat G$\alpha$i2 complemented only when substantially overexpressed, while G$\alpha$0 did not complement at all. Kang, et al., *Mol. Cell. Biol.*, (1990)10:2582). Consequently, with some foreign G$\alpha$ subunits, it is not feasible to simply replace the yeast G$\alpha$.

If the exogenous G protein coupled receptor is not adequately coupled to yeast G$\beta\gamma$ by the G$\alpha$ subunit natively associated with the receptor, the G$\alpha$ subunit may be modified to improve coupling. These modifications often will take the form of mutations which increase the resemblance of the G$\alpha$ subunit to the yeast G$\alpha$ while decreasing its resemblance to the receptor-associated G$\alpha$. For example, a residue may be changed so as to become identical to the corresponding yeast G$\alpha$ residue, or to at least belong to the same exchange group of that residue. After modification, the modified G$\alpha$ subunit might or might not be "substantially homologous" to the foreign and/or the yeast G$\alpha$ subunit.

The modifications are preferably concentrated in regions of the G$\alpha$ which are likely to be involved in G$\beta\gamma$ binding. In some embodiments, the modifications will take the form of replacing one or more segments of the receptor-associated G$\alpha$ with the corresponding yeast G$\alpha$ segment(s), thereby forming a chimeric G$\alpha$ subunit. (For the purpose of the appended claims, the term "segment" refers to three or more consecutive amino acids.) In other embodiments, point mutations may be sufficient.

This chimeric G$\alpha$ subunit will interact with the exogenous receptor and the yeast G$\beta\gamma$ complex, thereby permitting signal transduction. While use of the endogenous yeast G$\beta\gamma$ is preferred, if a foreign or chimeric G$\beta\gamma$ is capable of transducing the signal to the yeast effector, it may be used instead.

V. Pharmaceutical Preparations of Identified Agents

After identifying certain test peptides in the subject assay, e.g. as potential surrogate ligands, or receptor antagonists, the practitioner of the subject assay will continue to test the efficacy and specificity of the selected peptides both in vitro and in vivo. Whether for subsequent in vivo testing, or for administration to an animal as an approved drug, peptides identified in the subject assay, or peptidomimetics thereof, can be formulated in pharmaceutical preparations for in vivo administration to an animal, preferably a human.

The peptides selected in the subject assay, or a pharmaceutically acceptable salt thereof, may accordingly be formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the compound, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations". Based on the above, such pharmaceutical formulations include, although not exclusively, solutions or freeze-dried powders of the compound in association with one or more pharmaceutically acceptable vehicles or diluents, and contained in buffered media at a suitable pH and isosmotic with physiological fluids. In preferred embodiment, the peptide can be disposed in a sterile preparation for topical and/or systemic administration. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of compounds in isotonic solutions of the desired volume and include, but not exclusively, the use of buffered saline solutions with phosphate or citrate at suitable concentrations so as to obtain at all times isotonic pharmaceutical preparations of the desired pH, (for example, neutral pH).

Exemplification

The invention now being generally described, it will be more readily understood by reference to the following examples which are included merely for purposes of illustration of certain aspects and embodiments of the present invention, and are not intended to limit the invention.

As shown in FIG. 1, pAM6 M13/COS peptide expression plasmid is designed to have distinct functions in prokaryotic and eukaryotic cells. In prokaryotic cells the plasmid functions in the display mode, which directs the display of encoded peptides on the surface of the M13 phage within which it is packaged. The peptides are displayed as fusions with the major M13 capsid protein pVII. The-depicted elements which enable this mode are as follows: lac, the prokaryotic promoter; preIII signal, the periplasmic targeting signal sequence from M13 geneIII (the top vertical arrows which follow indicate cleavage sites for the signal peptidase); random peptide, the random or specific coding sequence of the peptide to be fused to an M13 coat protein;

M13 pVIII, the coding sequence of the pVIII coat protein of M13 (the STOP above it represents the stop codon and prokaryotic transcriptional terminator); ApR, the β-lactamase gene which allows ampicillin selection for cells carrying the plasmid; pUC ori, replication origin which directs high copy number replication of the plasmid within *E. coli*; M13(−) ori, replication origin and packaging signal which, in the presence of M13 helper phage, allows generation of single stranded DNA, and directs its packaging into phage particles.

In eukaryotic cells the plasmid functions in the secretion mode, which results in the secretion of the encoded peptide, apart from other sequences, into the extracellular media. The depicted elements which enable this mode are as follows: CMV enh/prom, the eukaryotic promoter; IgH secr.s., the immunoglobulin heavy chain signal sequence which directs extracellular secretion of proteins; random peptide, the random or specific coding sequence of the peptide to be secreted; SV40 polyA, RNA polyadenylation signal; globin splice donor/IgH splice acceptor pairs, direct processing of the RNA to a mature mRNA that is devoid of the unwanted intervening prokaryotic sequences; SV40 ori, origin of replication which results in high copy number replication of the plasmid in COS cells.

Other exemplary plasmids, pAM7 and pAM9 M13/COS peptide expression plasmids, are shown in FIG. 2. The difference between pAM7 and pAM9 is the M13 coat protein to which the peptide is fused in the display mode: pAM7 utilizes a pVIII fusion and pAM9 utilizes a pIII fusion, as indicated by M13 pVIII or pIII.

This plasmid design is identical to pAM6 (see FIG. 1) with the exception of the following modifications: The CMV enh/prom and lac promoters have been separated and placed adjacent to their respective eukaryotic IgH signal s and prokaryotic *E.coli* signal s signal sequences. The first pair of splice signals now functions to remove the lac promoter and *E.coli* signal sequence from the mRNA, as opposed to just the signal sequence in pAM6. In addition, the *E.coli* signal s sequence was created from concensus signal sequences, and into it's coding sequence the IgH splice acceptor sequence was silently engineered, which eliminates the addition of extra residues onto the amino terminus of the random peptide.

FIG. 3 illustrates yet another plasmid of the invention, the pAM8 M13/COS peptide expression plasmid. This plasmid design is identical to pAM6 (see FIG. 1) with the exception of the following modifications: Instead of using separate signal peptide sequences for the display and secretion modes, this design utilizes the β-lactamase signal sequence, which functions in both modes. This design eliminates the need for the first pair of splice signals.

Figure 4A:
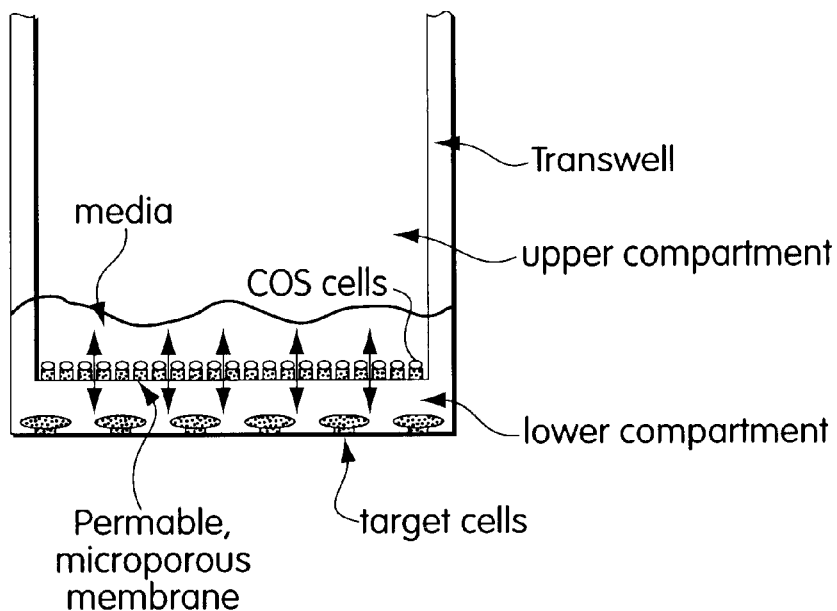
FIG. 4A: Transwell cell culture chamber.

An illustrative transwell cell culture chamber is shown in FIG. 4A. This illustration depicts the transwell system that is utilized in the secretion mode of the subject method. The lower compartment containing the target cells is a well in an ordinary tissue culture dish. The transwell, which fits into this well, is a chamber with solid sides and a permeable, microporous membrane bottom. The secreting COS cells are grown on this membrane through which their secreted peptides can diffuse and come into contact with the target cells.

Figure 4B:
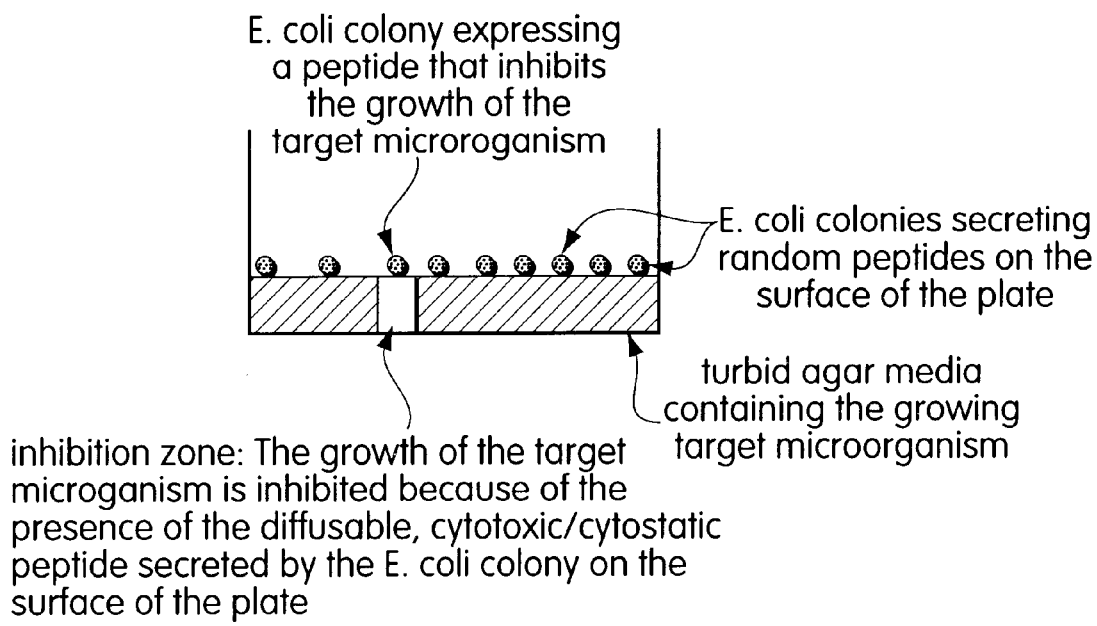
FIG. 4B: Indicator plate antimicrobial assay.

In other embodiments, the subject method is used as part of an indicator plate antimicrobial assay. FIG. 4B illustrates a method for identifying peptides with antimicrobial activity. Bacterial cells carrying plasmids that direct the secretion of test peptides are plated on top of an agar embedded culture of target microorganisms. Production of an inhibitory peptide by any of the bacterial colonies will result in an inhibition zone in the agar embedded target cell culture. This zone will be visualized as a clear area in the agar, due to the inability of the target cells to form a dense culture in the presence of the secreted peptide.

Figure 5:
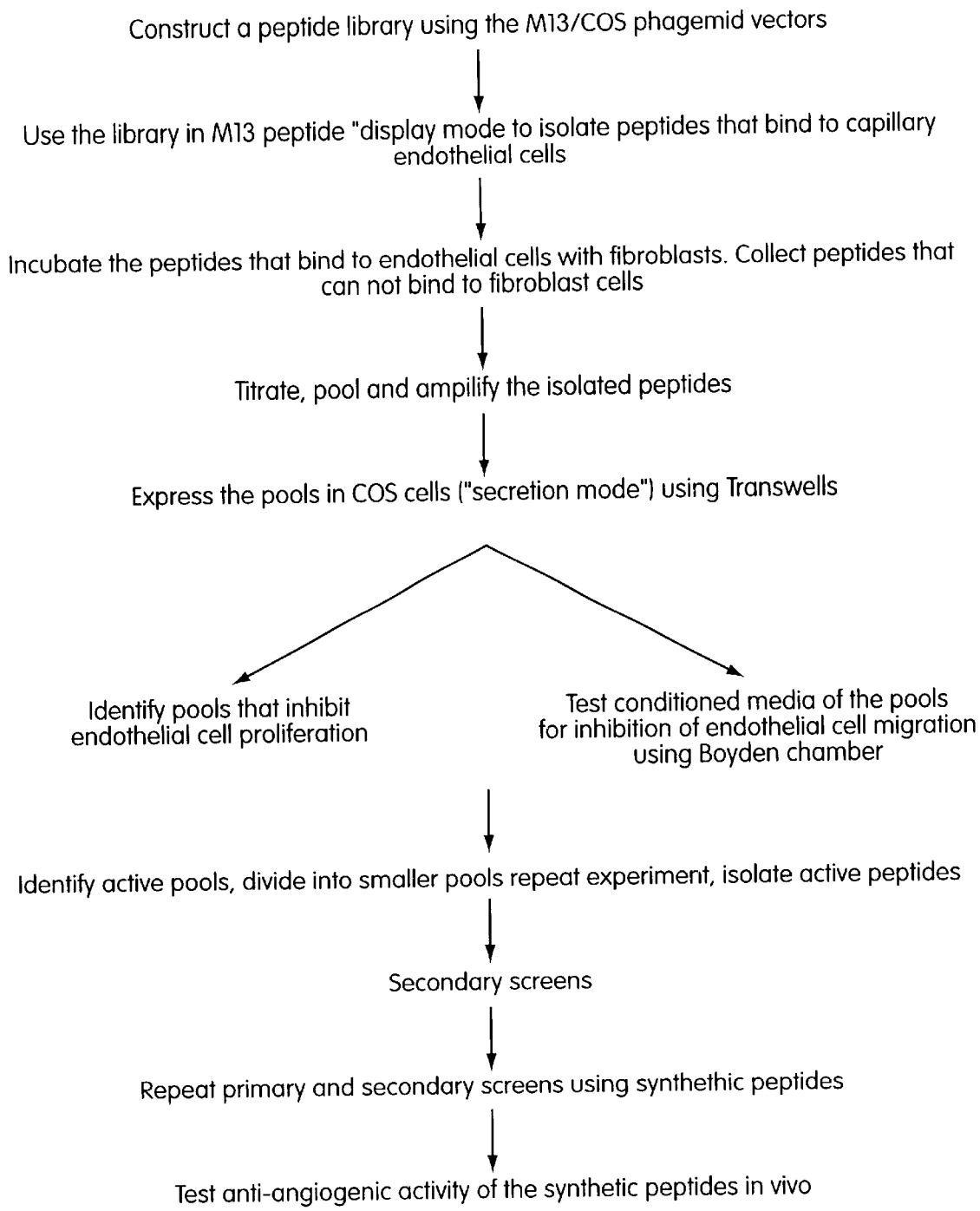
FIG. 5: Flowchart depicting utilization of the M13 display/COS secretion method for identification of anti-angiogenic peptides.

The method of the present invention has been utilized to identify anti-angiogenic peptides. FIG. 5 is a flowchart depicting utilization of the M13 display/COS secretion method for identification of anti-angiogenic peptides. FIG. 6 shows the sequence of a version of the pAM6 M13/COS peptide expression plasmid. In this example the random peptide, flanked by distinct BstX1 sites, is actually a Myc epitope-6xHis control peptide.

Figure 7:
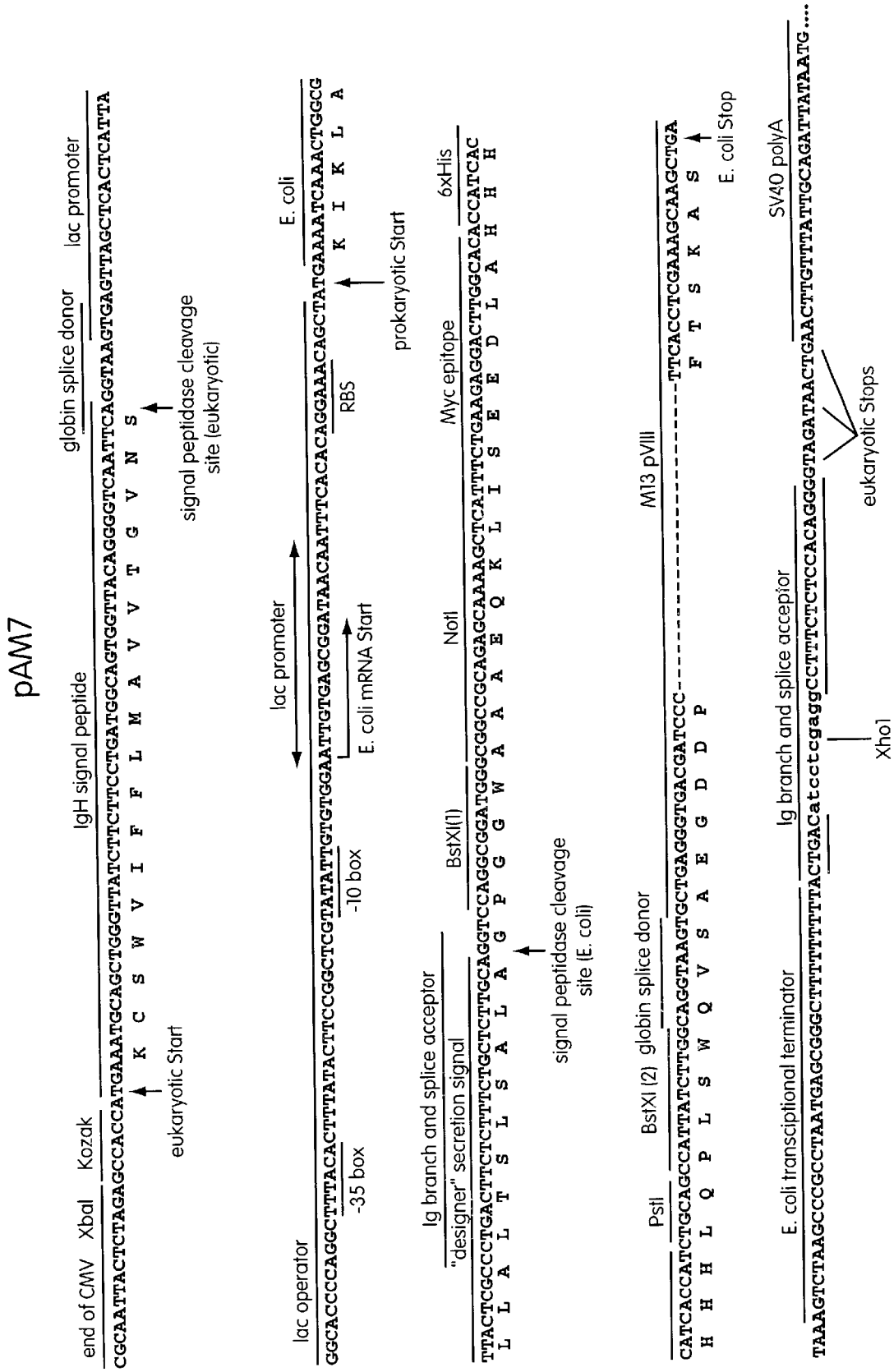
FIG. 7: Nucleotide level depiction of pAM7 M13/COS peptide expression plasmid.
Figure 8:
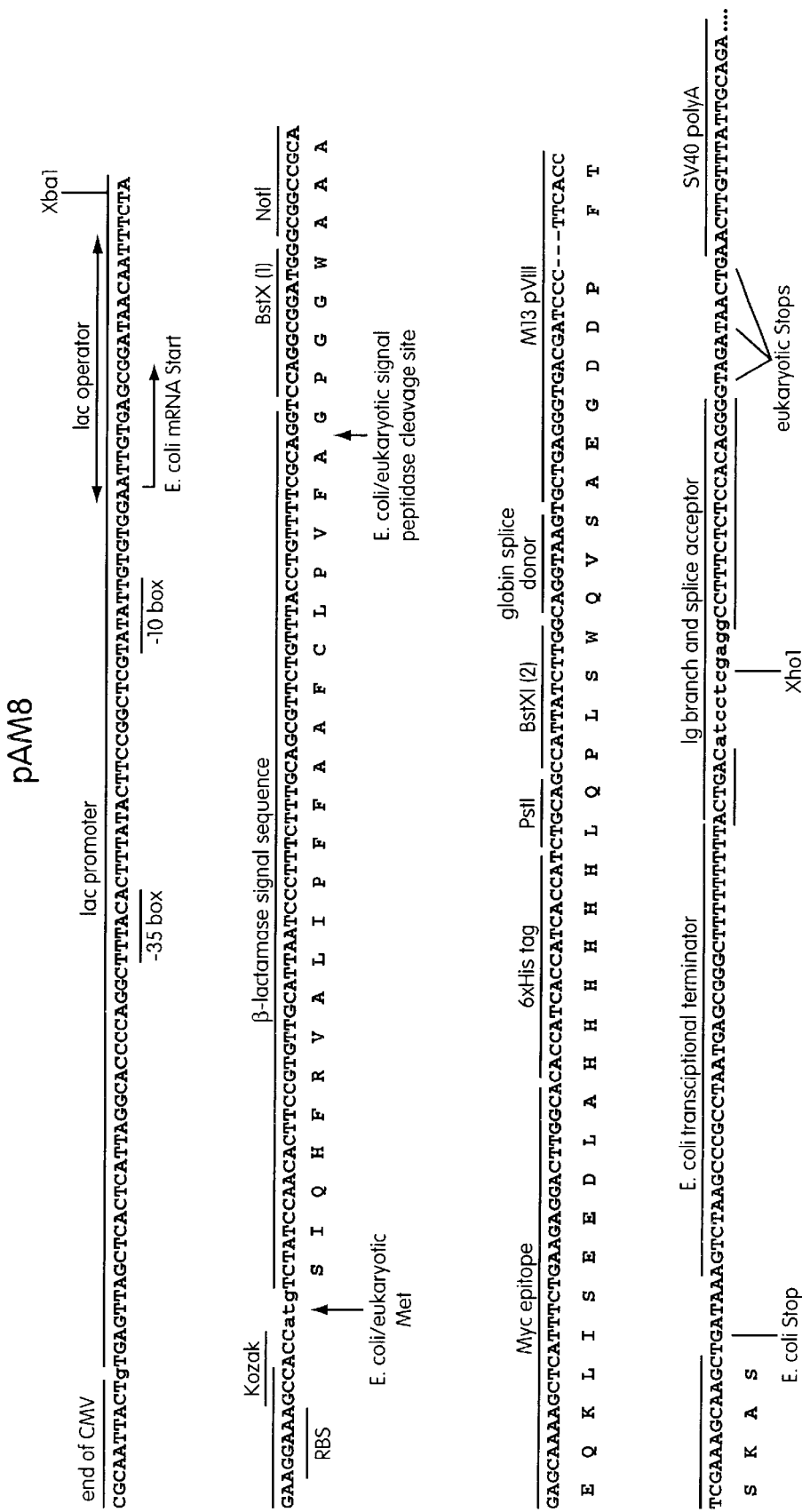
FIG. 8: Nucleotide level depiction of pAM8 M13/COS peptide expression plasmid.

FIGS. 6, 7 and 8 each provide a more detailed look at the functional elements of the pAM6, pAM7 and pAM8 M13/COS plasmid shown in FIGS. 1, 2 and 3 respectively. In each of these example the random peptide, flanked by distinct BstX1 sites, is actually a Myc epitope-6xHis control peptide.

To test each of the plasmids, *E. coli* were transformed with the negative control pLITMUS plasmid and the Myc epitope-6xHis encoding plasmids: pAM6, pAM7 and pAM8. The cells were grown at 37° C. to log phase and induced with 0.1 mM IPTG for 3 hours (+) or grown for 3 hours in the absence of IPTG (−). Whole cell lysates were separated by electrophoresis on a 16% tricine SDS-PAG, and immunoblotted with anti-myc antibody.

Figure 9:
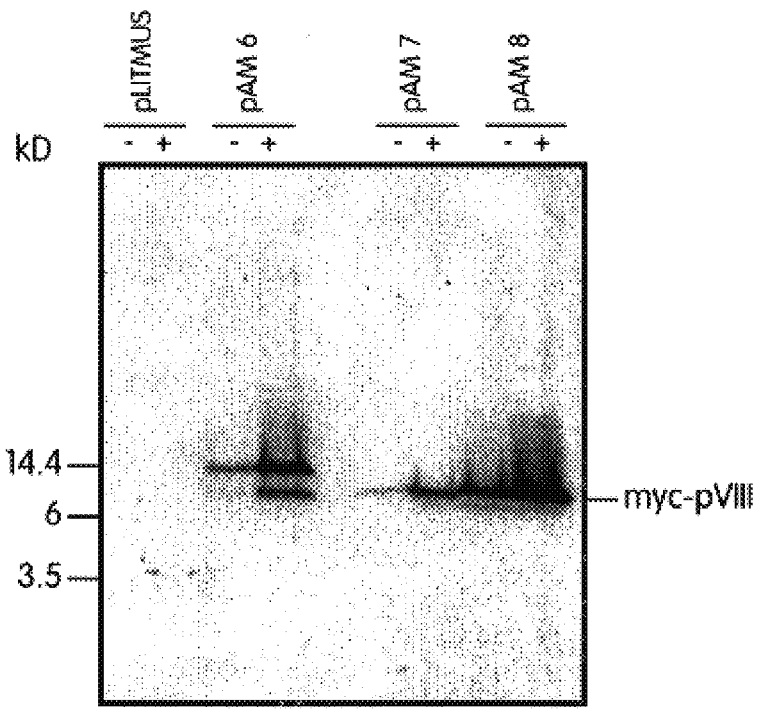
FIG. 9: Expression of the Myc epitope-pVIII in *E. coli*.

The results (FIG. 9) demonstrate that each of the M13/COS vectors express the Myc-6xHis-pVIII fusion protein, and that the products of pAM7 and pAM8 appear to be properly processed. However, the apparent molecular weight of the peptides secreted from pAM6 indicates a signal peptide processing problem, i.e., the higher molecular weight species corresponds to the expected size of a peptide without the signal peptides cleaved.

The incorporation of myc-6xHis-pVIII fusion protein into phagemid capsids was tested by anti-myc western blotting. *E. coli* were transformed with the negative control pLITMUS plasmid and the Myc epitope-6xHis encoding plasmids: pAM6, pAM7 and pAM8. The cells were grown at 37° C. to log phase, induced with 0.1 mM IPTG, infected with M13 helper phage and grown overnight. Phagemids contained in the culture media supernatant were separated by electrophoresis on a 16% tricine SDS-PAG, and immunoblotted with anti-myc antibody.

Figure 10:
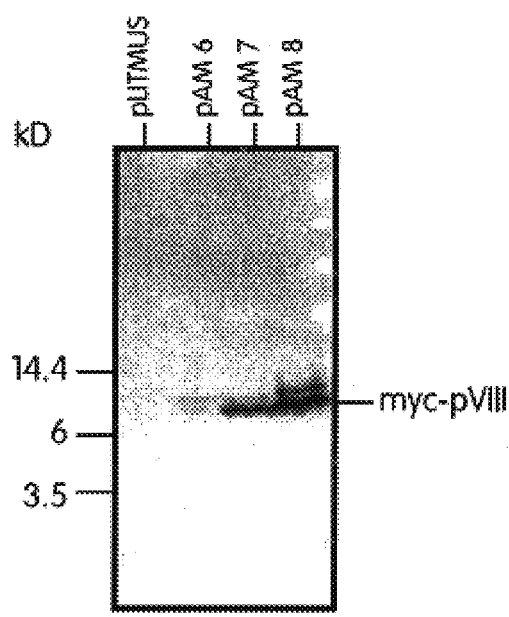
FIG. 10: Anti-myc western blot detection of myc-pVIII incorporated into phagemid capsids.

FIG. 10 demonstrates that the pAM7 and pAM8 vectors result in properly processed Myc-6xHis-pVIII fusion protein being incorporated into the capsid. Very little fusion protein is incorporated into the capsid of phagemids produced by pAM6 transformants, and nothing is detected in the negative control pLITMUS lane.

The ratio of native pVIII versus myc-6xHis-pVIII proteins in phagemid capsids was also determined. As above, *E. coli* were transformed with the negative control pLITMUS plasmid and the Myc epitope-6xHis encoding plasmids: pAM6, pAM7 and pAM8. The cells were grown at 37° C. to log phase, induced with 0.1 mM IPTG, infected with M13 helper phage and grown overnight. Phagemids contained in the culture media supernatant were separated by electrophoresis on a 16% tricine SDS-PAG, and stained with coomassie blue.

We observed that pAM7 and pAM8 vectors result in properly processed Myc-6xHis-pVIII fusion protein being incorporated into the capsid at a ratio of 1–10% of native pVIII. No fusion protein is detected in the pAM6 or pLITMUS lanes.

Phagemids produced as described above were also tested for itration of plaque and colony forming units generated upon phagemid rescue by serially dilution and infection into log phase *E. coli*. See FIG. 11. Infected cells were either plated on soft agar to detect plaque forming units (p.f.u.), or on ampicillin to determine colony forming units (c.f.u.). c.f.u. represent those phage which have packaged a plasmid DNA, whereas p.f.u. represent phage which have packaged helper a phage genome DNA.

Figures 11, 12:
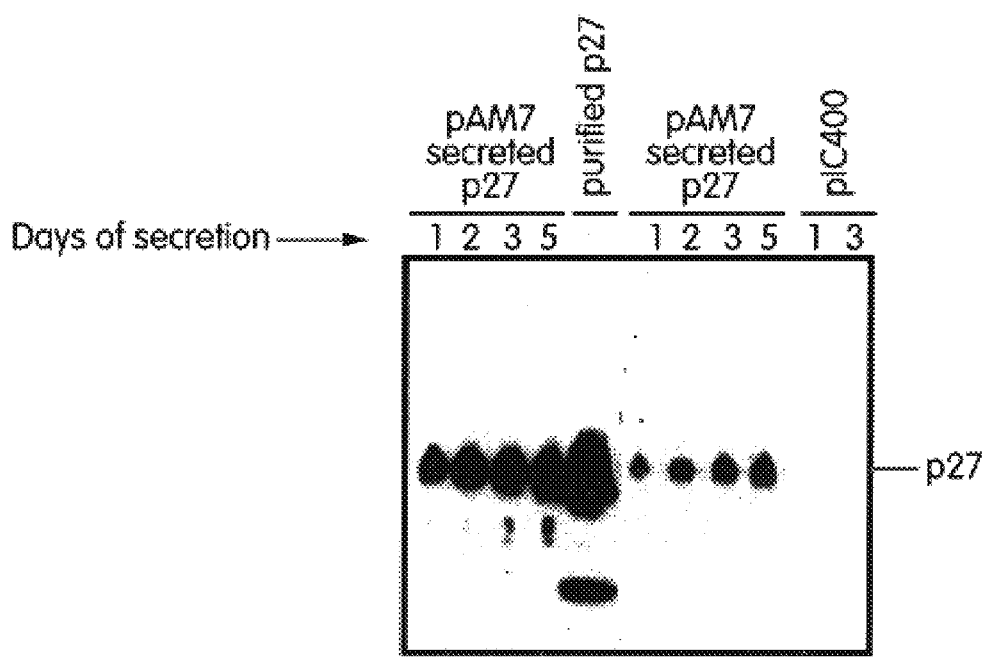
FIG. 11: Titration of plaque and colony forming units generated upon phagemid rescue.
FIG. 12: Secretion of M13/COS plasmid encoded proteins from COS-7 cells.

The secretion of M13/COS plasmid encoded proteins from COS-7 cells, e.g., in the secretion mode, is examined. COS-7 cells were transfected with pIC400 negative control plasmid and with pAM7 and pAM8 plasmids, which encode p27 in the random peptide insertion site. The normally intracellular p27 was chosen for this experiment to enable efficient western blot detection of the secreted protein in the cell media. 20 ul aliquots of media were collected on days 1, 2, 3 and 5 following transfection, separated by SDS-PAGE and immunoblotted with anti-p27 antibody. As shown in FIG. 12, the level of secreted protein in the media increased over the time of the experiment for both pAM7 and pAM8, although there is considerably more p27 produced by the pAM7 vector design. No p27 is detected with pIC400 negative control. Purified p27 is included as a size marker.

Figure 13:
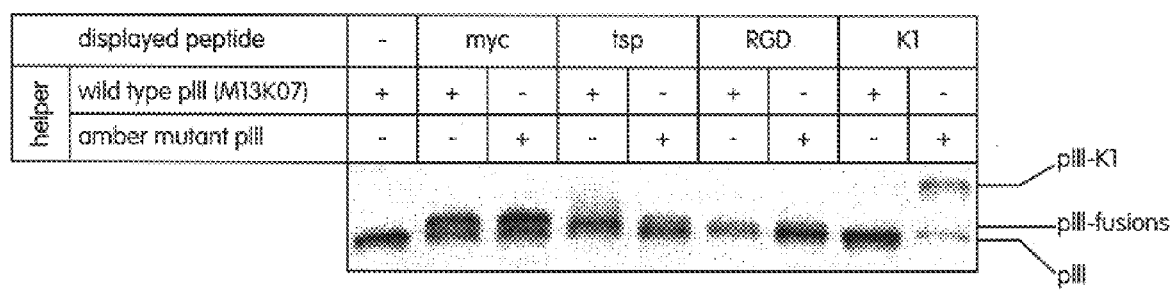
FIG. 13: Anti-pIII western blot detection of peptides incorporated into M13 phagemid capsids as pIII fusions

FIG. 13 shows an anti-pIII western blot detection of peptides incorporated into M13 phagemid capsids as pIII fusions. Briefly, oligonucleotides encoding the the Myc epitope-6xHis peptide, a thrombospondin derived peptide (tsp: SPWSSASVTCGDGVITRIR), an ($\alpha_v\beta_3$ integrin binding peptide containing the RGD motif (CDCRGDCFC) and the first kringle domain of angiostatin (K1: 80 amino acids) were inserted between the the BstXI sites of pAM9. In *E. coli*, the plasmids direct the expression of the peptide-pIII fusion proteins. For phagemid production the cells were grown at 37° C. to log phase, induced with 0.1 mM IPTG, infected with M13 helper phage or an M13 helper phage that carries an amber mutation in the pIII gene and grown overnight. Phagemids contained in the culture media supernatant were separated by electrophoresis on a 16% tricine SDS-PAG, and immunoblotted with anti-pIII antibody. As a control M13K07 phage particle were used. The lower bands correspond to wild type pIII proteins while the upper, higher molecular weight bands correspond to the peptide-pIII fusion proteins.

The data demonstrate that the pAM9 derived vectors express the predicted peptides as pIII fusions and the fusion proteins being incorporated into the capsid of M13 phagemids.

Figure 14:
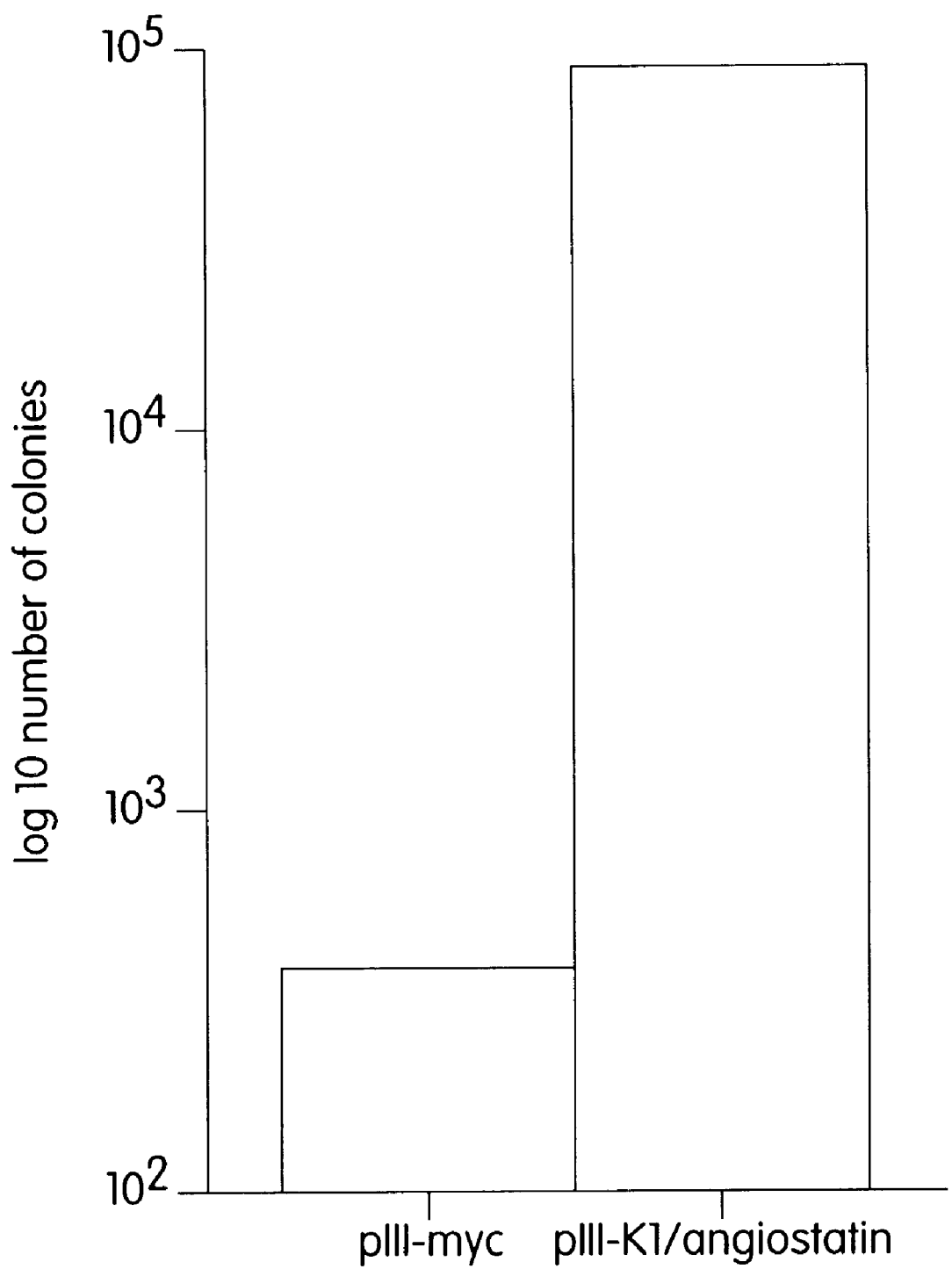
FIG. 14: Specific binding of pAM9-K1 phagemids to bovine capillary endothelial cells

We observed specific binding of pAM9-K1 phagemids to bovine capillary endothelial cells. See FIG. 14. Phagemid particles that display either the Myc epitope-6xHis peptide (pAM9-myc; negative control) or the first kringle domain of angiostatin (pAM9-K1, positive control) as pIII fusions were used to test the specificity of phagemid binding to bovine capillary endothelial (BCE) cells. >90% confluent BCE cells in a well of a 6 well plate were incubated with ~5×10$^{12}$ M13K07 p.f.u./well in 2.5 ml of Peptide binding buffer (1×PBS, 1 mM CaCl$_2$, 10 mM MgCl$_2$, 0.1% BSA) for 30 minutes at 37 C. 10$^8$ c.f.u. pAM9-myc or pAM9-K1 phagemids were added to the mix and the incubation continued for 45 minutes at 37 C. Excess phagemids were removed by washing the cells 5×5 ml Washing buffer (2×PBS, 1 mM CaCl$_2$, 10 mM MgCl$_2$, 0.1% BSA) and phagemids bound to BCE cells were eluted by 2×1 ml 0.1N HCl pH:2.2 that were neutralized by the addition of 1 ml 1M Tris/Cl pH:8.0. The number of phagemids in the elution buffer was determined by infecting TG1 cells with aliqouts of the eluates and selecting pAM9-myc or pAM9-K1 transformants on LB+Amp (M13K07 phage do not form colonies on LB+Amp).

The data demonstrate the feasibility to enrich random peptide libraries in the display mode for peptides that specifically bind to endothelial cells.

Figure 15A:
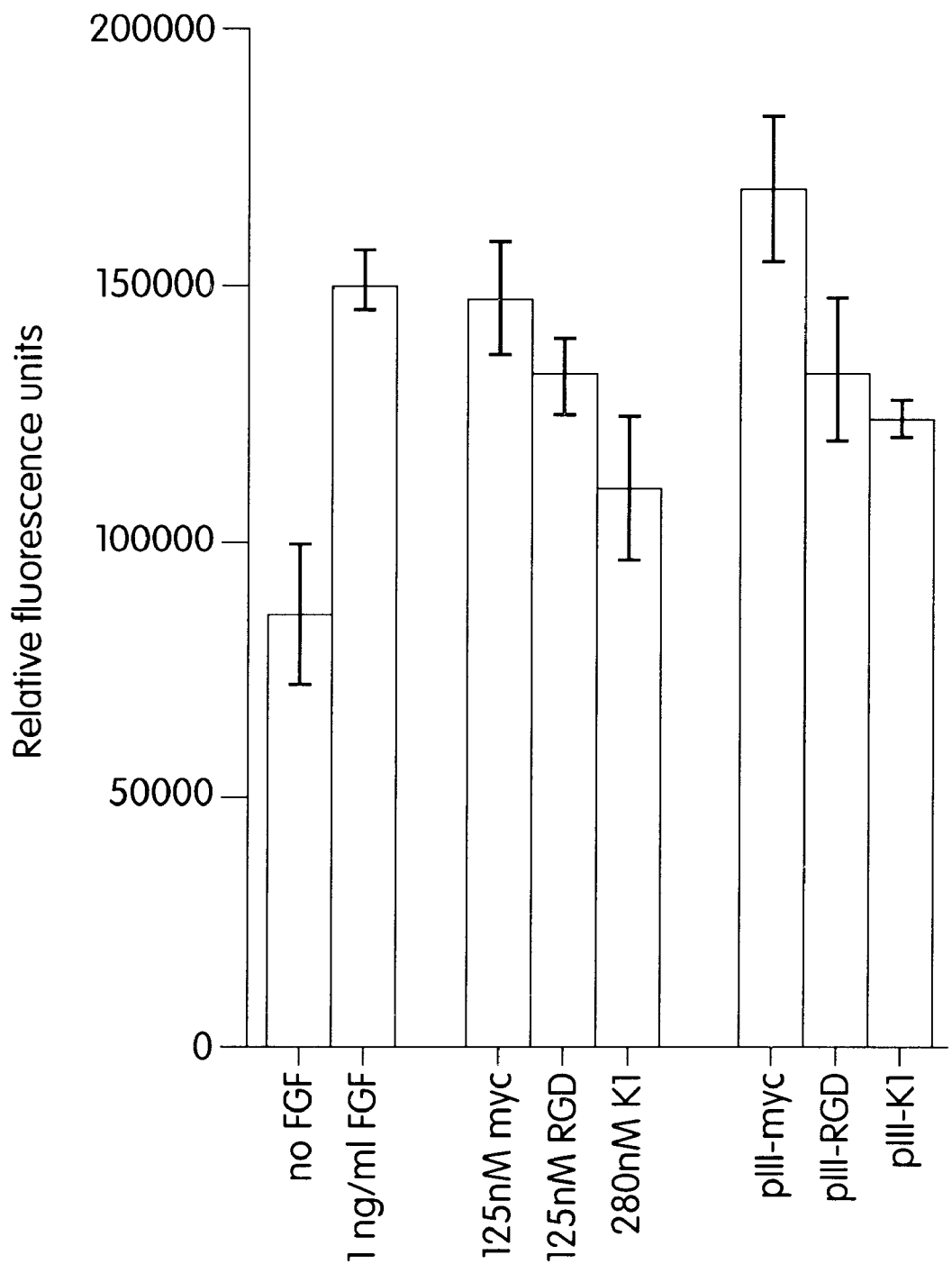
FIG. 15: Inhibition BCE cell proliferation in Transwells by peptides secreted from COS-7 cells
Figure 15B:
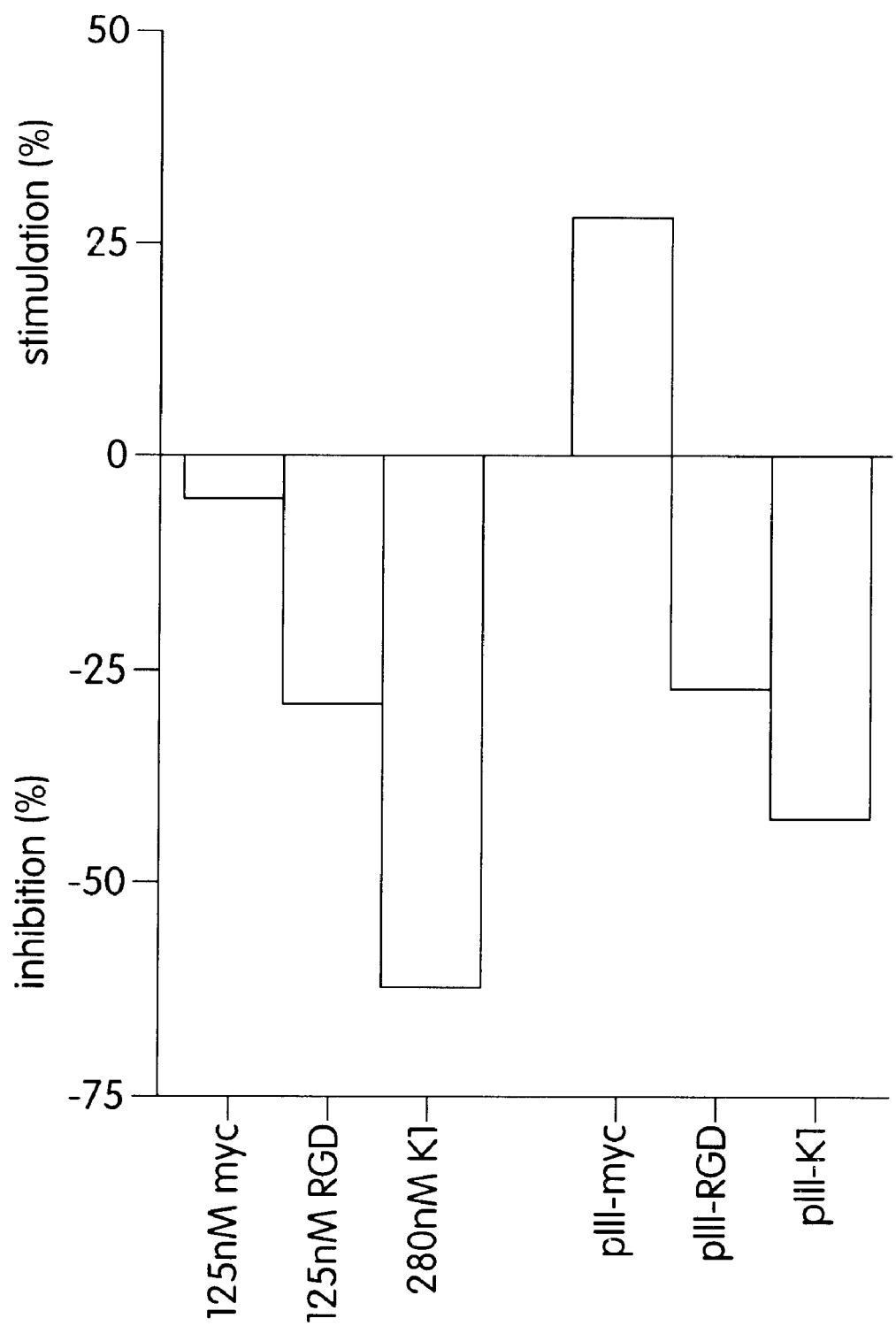

FIG. 15 shows inhibition of BCE cell proliferation in transwells by peptides secreted from COS-7 cells. COS-7 cells were transfected with pAM9-myc, pAM9-RGD and pAM9-K1 plasmids, respectively, that direct the expression and secretion of the Myc epitope-6xHis, the RGD and the angiostatin first kringle domain peptides. The transfected COS-7 cells were co-incubated in Transwells with BCE cells whose proliferation was stimulated by 1 ng/ml bFGF. As controls, untransfected COS-7 cells and bFGF stimulated BCE cells were similarly co-incubated and synthetic Myc-6xHis and RGD peptides as well as purified K1 were added to the media at the indicated concentrations. The proliferation of the bFGF stimulated BCE cells were measured 72 hrs later using the fluorescent CyQUANT proliferation kit (Molecular Probes).

The synthetic RGD peptide and the purified K1 as well as the COS-7 secreted RGD and K1 peptides inhibited bFGF stimulated BCE cell proliferation (positive controls). The negative control Myc epitope-6xHis peptide did not have inhibitory effect on BCE proliferation. The data demonstrate the feasibility of screening random peptide libraries in the secretion mode for peptides that inhibit the proliferation of endothelalial cells.

All of the above-cited references and publications are hereby incorporated by reference.

Equivalents

Those skilled in the art will recognize, or be able to ascertain using no more than routine experimentation, numerous equivalents to the specific method and reagents described herein. Such equivalents are considered to be within the scope of this invention and are covered by the following claims.

What is claimed is:

1. A method for identifying a peptide with a selected biological activity, comprising the steps of:
   (i) providing a peptide display library comprising a variegated population of test peptides expressed on the surface of a population of display packages each of the test peptide being encoded by a chimeric gene;
   (ii) isolating, in a display mode, from the peptide display library, a sub-population of display packages enriched for test peptides which have a desired binding specificity or affinity for a cell or a cell component,
   (iii) expressing, in a secretion mode, chimeric gene associated with the subpopulation of display packages in eukaryotic cells under conditions wherein the test peptides are secreted and are free of the display packages; and
   (iv) assessing the ability of the secreted test peptides to regulate a biological process in a target cell, thereby identifying peptides with a selected biological activity,
wherein each chimeric gene comprises (i) a coding sequence for the test peptide, (ii) a coding sequence for a surface protein of the display package for displaying the test peptides on the surface of a population of display packages, and (iii) RNA splice sites flanking the coding sequence for the surface protein, wherein, in the display mode, the chimeric gene is expressed as fusion protein including the test peptide and the surface protein, whereas in the secretion mode, the test peptide is expressed without the surface protein as a result of the coding sequence for the surface protein being removed by RNA splicing, and
wherein the chimeric gene is included in a vector which further includes an origin of replication for a prokaryotic cell, a transcriptional regulatory element for expressing the chimeric gene in a prokaryotic cell, a transcriptional regulatory element for expressing the chimeric gene in a eukaryotic cell, a secretion signal, a coding sequence for a phage coat protein, a marker gene, and a phage origin of replication.

2. The method of claim 1, wherein the peptide display library is a phage display library.

3. The method of claim 2, wherein the display packages of the phage display library are phage particles selected from a group consisting of M13, f1, fd, If1, Ike, Xf, Pf1, Pf3, λ, T4, T7, P2, P4, φX-174, MS2 and f2.

4. The method of claim 2, wherein the phage display library is generated with a filamentous bacteriophage specific for *Escherichia coli* and the phage coat protein is coat protein III or coat protein VIII.

5. The method of claim 4, wherein the filamentous bacteriophage is selected from a group consisting of M13, fd, and f1.

6. The method of claim 1, wherein the peptide display library is a bacterial cell-surface display library or a bacterial spore display library.

7. The method of claim 2, wherein isolating said subpopulation of display packages comprises affinity separation of test peptides which specifically bind the cell or cell component from test peptides which do not bind to the cell or cell component.

8. The method of claim 7, wherein the differential binding means comprises panning the peptide display library on whole cells.

9. The method of claim 7, wherein the differential binding means comprises an affinity chromatographic means in which a component of a cell is provided as part of an insoluble matrix.

10. The method of claim 9, wherein the insoluble matrix comprises a cell surface protein attached to a polymeric support.

11. The method of claim 7, wherein the differential binding means comprises immunoprecipitating the display packages.

12. The method of claim 1, wherein the display mode enriches for test peptides which bind to a cell-type specific marker.

13. The method of claim 1, wherein the display mode enriches for test peptides which bind to a cell surface receptor protein.

14. The method of claim 13, wherein the receptor protein is a G-protein coupled receptor.

15. The method of claim 14, wherein the G-protein coupled receptor is selected from the group consisting of: a chemoattractant peptide receptor, a neuropeptide receptor, a light receptor, a neurotransmitter receptor, a cyclic AMP receptor, and a polypeptide hormone receptor.

16. The method of claim 14, wherein the G-protein coupled receptor is selected from the group consisting of: α1A-adrenergic receptor, α1B-adrenergic receptor, α2-adrenergic receptor, α2B-adrenergic receptor, β1-adrenergic receptor, β2-adrenergic receptor, β3-adrenergic receptor, m1 acetylcholine receptor (AChR), m2 AChR, m3 AChR, m4 AChR, m5 AChR, D1 dopamine receptor, D2 dopamine receptor, D3 dopamine receptor, D4 dopamine receptor, D5 dopamine receptor, A1 adenosine receptor, A2b adenosine receptor, 5-HT1a, 5-HT1b, 5HT1-like, 5-HT1d, 5HT1d-like, 5HT1d beta, substance K (neurokinin A), fMLP receptor, fMLP-like receptor, angiotensin II type 1, endothelin ETA, endothelin ETB, thrombin, growth hormone-releasing hormone (GHRH), vasoactive intestinal peptide, oxytocin, somatostatin SSTR1 and SSTR2, SSTR3, cannabinoid, follicle stimulating hormone (FSH), leutropin (LH/HCG), thyroid stimulating hormone (TSH), thromboxane A2, platelet-activating factor (PAF), C5a anaphylatoxin, Interleukin 8 (IL-8) IL-8RA, IL-8RB, Delta Opioid, Kappa Opioid, mip-1/RANTES, Rhodopsin, Red opsin, Green opsin, Blue opsin, metabotropic glutamate mGluR1-6, histamine H2, ATP, neuropeptide Y, amyloid protein precursor, insulin-like growth factor II, bradykinin, gonadotropin-releasing hormone, cholecystokinin, melanocyte stimulating hormone receptor, antidiuretic hormone receptor, glucagon receptor, and adrenocorticotropic hormone II.

17. The method of claim 13, wherein the receptor protein is a receptor tyrosine kinase.

18. The method of claim 17, wherein the receptor tyrosine kinase is an EPH receptor.

19. The method of claim 18, wherein the receptor is selected from the group consisting of: eph, elk, eck, sek, mek4, hek, hek2, eek, erk, tyro1, tyro4, tyro5, tyro6, tyro11, cek4, cek5, cek6, cek7, cek8, cek9, cek10, bsk, rtk1, rtk2, rtk3, myk1, myk2, ehk1, ehk2, pagliaccio, htk, erk and nuk receptors.

20. The method of claim 13, wherein the receptor protein is a cytokine receptor.

21. The method of claim 13, wherein the receptor protein is an MIRR receptor.

22. The method of claim 13, wherein the receptor protein is an orphan receptor.

23. The method of claim 1, wherein the peptide display library includes at least $10^3$ different test peptides.

24. The method of claim 1, wherein the test peptides are 4–20 amino acid residues in length.

25. The method of claim 1, wherein the target cell is a eukaryotic cell.

26. The method of claim 25, wherein the eukaryotic cell is a mammalian cell.

27. The method of claim 26, wherein the mammalian cell is a human cell.

28. The method of claim 1, wherein the biological process includes a change in cell proliferation, cell differentiation or cell death.

29. The method of claim 1, wherein the biological process is detected by changes in intracellular calcium mobilization.

30. The method of claim 1, wherein the biological process is detected by changes in intracellular protein phosphorylation.

31. The method of claim 1, wherein the biological process is detected by changes in phospholipid metabolism.

32. The method of claim 1, wherein the biological process is detected by changes in expression of cell-specific marker genes.

33. The method of claim 13, wherein the target cell further comprises a reporter gene construct containing a reporter gene in operative linkage with one or more transcriptional regulatory elements responsive to the signal transduction activity of the cell surface receptor protein, expression of the reporter gene providing the detectable signal.

34. The method of claim 32, wherein the reporter gene encodes a gene product that gives rise to a detectable signal selected from the group consisting of: color, fluorescence, luminescence, cell viability, relief of a cell nutritional requirement, cell growth, and drug resistance.

35. The method of claim 34, wherein the reporter gene encodes a gene product selected from the group consisting of chloramphenicol acetyl transferase, beta-galactosidase and secreted alkaline phosphatase.

36. The method of claim 34, wherein the reporter gene encodes a gene product which confers a growth signal.

37. The method of claim 1, wherein the secretion mode includes expression of the test peptides by a host cell co-cultured with the target cell.

38. The method of claim 31, wherein the co-cultured host and target cells are separated by a membrane which is permeable to the test peptide.

39. The method of claim 1, wherein the secretion mode comprises assessing the ability of the secreted test peptides to inhibit the biological activity of an exogenously added compound on the target cells.

40. The method of claim 1, wherein: in step (ii), display packages which bind to endothelial cells are isolated; and in step (iv), the ability of the secreted test peptides to inhibit proliferation of endothelial cells is assessed.

41. The method of claim 40, wherein: in step (iv), the ability of the secreted test peptides to inhibit proliferation of endothelial cells in the presense of an angiogenic amount of an endogenous growth factor is assessed.

42. A method for preparing a therapeutic composition, comprising
 (i) identifying a test peptide with a selected biological activity according to the method of claim 1, and
 (ii) combining a pharmaceutically acceptable carrier with the peptide.

* * * * *

SEQUENCE LISTING

<160> NUMBER OF SEQ ID NOS: 8

<210> SEQ ID NO 1
<211> LENGTH: 527
<212> TYPE: DNA
<213> ORGANISM: Artificial Sequence

```
<220> FEATURE:
<223> OTHER INFORMATION: Description of Artificial Sequence: pAM6
      M13/COS peptide expression plasmid
<220> FEATURE:
<221> NAME/KEY: CDS
<222> LOCATION: (124..222, 226..417)

<400> SEQUENCE: 1
cgcaattact gtgagttagc tcactcatta ggcaccccag gctttacact ttatacttcc    60
ggctcgtata ttgtgtggaa ttgtgagcgg ataacaattt ctagaaggaa acaggtaagt   120 atg aaa aaa tta tta ttc gca att cct tta gtt gtt cct ttc tat tct    168
    Lys Lys Leu Leu Phe Ala Ile Pro Leu Val Val Pro Phe Tyr Ser
    1               5                   10                  15 cac tcc gct gaa tta ctg aca tcc act ttg cct ttc tct cca cag ggg    216
His Ser Ala Glu Leu Leu Thr Ser Thr Leu Pro Phe Ser Pro Gln Gly
                20                  25                  30 gcc acc atg aaa tgc agc tgg gtt atc ttc ttc ctg atg gca gtg gtt    264
Ala Thr     Lys Cys Ser Trp Val Ile Phe Phe Leu Met Ala Val Val
                35                  40                  45 aca ggg gtc aat tca gca cca ggc gga tgg gcg gcc gca gag caa aag    312
Thr Gly Val Asn Ser Ala Pro Gly Gly Trp Ala Ala Ala Glu Gln Lys
            50                  55                  60 ctc att tct gaa gag gac ttg gca cac cat cac cat cac cat ctg cag    360
Leu Ile Ser Glu Glu Asp Leu Ala His His His His His His Leu Gln
        65                  70                  75 cca tta tct tgg cag gta agt gct gag ggt gac gat ccc ttc acc tcg    408
Pro Leu Ser Trp Gln Val Ser Ala Glu Gly Asp Asp Pro Phe Thr Ser
    80                  85                  90 aaa gca agc tgataaagtc taagcccgcc taatgagcgg gctttttttt            457
Lys Ala Ser
 95 tactgacatc ctcgaggcct ttctctccac agggggtagat aactgaactt gtttattgca   517 gattataatg                                                          527

<210> SEQ ID NO 2
<211> LENGTH: 97
<212> TYPE: PRT
<213> ORGANISM: Artificial Sequence
<220> FEATURE:
<223> OTHER INFORMATION: Description of Artificial Sequence: pAM6

<400> SEQUENCE: 2

Lys Lys Leu Leu Phe Ala Ile Pro Leu Val Val Pro Phe Tyr Ser His
1               5                   10                  15

Ser Ala Glu Leu Leu Thr Ser Thr Leu Pro Phe Ser Pro Gln Gly Ala
            20                  25                  30

Thr Lys Cys Ser Trp Val Ile Phe Phe Leu Met Ala Val Val Thr Gly
        35                  40                  45

Val Asn Ser Ala Pro Gly Gly Trp Ala Ala Ala Glu Gln Lys Leu Ile
    50                  55                  60

Ser Glu Glu Asp Leu Ala His His His His His Leu Gln Pro Leu
65                  70                  75                  80

Ser Trp Gln Val Ser Ala Glu Gly Asp Asp Pro Phe Thr Ser Lys Ala
                85                  90                  95

Ser

<210> SEQ ID NO 3
<211> LENGTH: 488
<212> TYPE: DNA
```

<213> ORGANISM: Artificial Sequence
<220> FEATURE:
<223> OTHER INFORMATION: Description of Artificial Sequence: pAM7
     M13/COS peptide expression plasmid
<220> FEATURE:
<221> NAME/KEY: CDS
<222> LOCATION: (25..78, 193..378)

<400> SEQUENCE: 3

```
cgcaattact ctagagccac catg aaa tgc agc tgg gtt atc ttc ttc ctg        51
                          Lys Cys Ser Trp Val Ile Phe Phe Leu
                           1               5 atg gca gtg gtt aca ggg gtc aat tca ggtaagtgag ttagctcact             98
Met Ala Val Val Thr Gly Val Asn Ser
 10              15 cattaggcac cccaggcttt acactttata cttccggctc gtatattgtg tggaattgtg    158
agcggataac aatttcacac aggaaacagc tatg aaa atc aaa ctg gcg tta        210
                                     Lys Ile Lys Leu Ala Leu
                                      20 ctc gcc ctg act tct ctt tct gct ctt gca ggt cca ggc gga tgg gcg      258
Leu Ala Leu Thr Ser Leu Ser Ala Leu Ala Gly Pro Gly Gly Trp Ala
 25                  30                  35                  40 gcc gca gag caa aag ctc att tct gaa gag gac ttg gca cac cat cac      306
Ala Ala Glu Gln Lys Leu Ile Ser Glu Glu Asp Leu Ala His His His
                 45                  50                  55 cat cac cat ctg cag cca tta tct tgg cag gta agt gct gag ggt gac      354
His His His Leu Gln Pro Leu Ser Trp Gln Val Ser Ala Glu Gly Asp
                 60                  65                  70 gat ccc ttc acc tcg aaa gca agc tgataaagtc taagcccgcc taatgagcgg    408
Asp Pro Phe Thr Ser Lys Ala Ser
                 75              80 gcttttttttt tactgacatc ctcgaggcct ttctctccac aggggtagat aactgaactt   468
gtttattgca gattataatg                                                488
```

<210> SEQ ID NO 4
<211> LENGTH: 80
<212> TYPE: PRT
<213> ORGANISM: Artificial Sequence
<220> FEATURE:
<223> OTHER INFORMATION: Description of Artificial Sequence: pAM7

<400> SEQUENCE: 4

```
Lys Cys Ser Trp Val Ile Phe Phe Leu Met Ala Val Val Thr Gly Val
 1               5                  10                  15

Asn Ser Lys Ile Lys Leu Ala Leu Leu Ala Leu Thr Ser Leu Ser Ala
             20                  25                  30

Leu Ala Gly Pro Gly Gly Trp Ala Ala Ala Glu Gln Lys Leu Ile Ser
         35                  40                  45

Glu Glu Asp Leu Ala His His His His His His Leu Gln Pro Leu Ser
     50                  55                  60

Trp Gln Val Ser Ala Glu Gly Asp Asp Pro Phe Thr Ser Lys Ala Ser
 65                  70                  75                  80
```

<210> SEQ ID NO 5
<211> LENGTH: 426
<212> TYPE: DNA
<213> ORGANISM: Artificial Sequence
<220> FEATURE:
<223> OTHER INFORMATION: Description of Artificial Sequence: pAM8
     M13/COS peptide expression plasmid
<220> FEATURE:
<221> NAME/KEY: CDS

<222> LOCATION: (121)..(324)

<400> SEQUENCE: 5

```
cgcaattact gtgagttagc tcactcatta ggcaccccag gctttacact ttatacttcc      60
ggctcgtata ttgtgtggaa ttgtgagcgg ataacaattt ctagaaggaa agccaccatg     120 tct atc caa cac ttc cgt gtt gca tta atc cct ttc ttt gca gcg ttc      168
Ser Ile Gln His Phe Arg Val Ala Leu Ile Pro Phe Phe Ala Ala Phe
 1               5                  10                  15 tgt tta cct gtt ttc gca ggt cca ggc gga tgg gcg gcc gca gag caa     216
Cys Leu Pro Val Phe Ala Gly Pro Gly Gly Trp Ala Ala Ala Glu Gln
             20                  25                  30 aag ctc att tct gaa gag gac ttg gca cac cat cac cat cac ctg         264
Lys Leu Ile Ser Glu Glu Asp Leu Ala His His His His His Leu
         35                  40                  45 cag cca tta tct tgg cag gta agt gct gag ggt gac gat ccc ttc acc     312
Gln Pro Leu Ser Trp Gln Val Ser Ala Glu Gly Asp Asp Pro Phe Thr
     50                  55                  60 tcg aaa gca agc tgataaagtc taagcccgcc taatgagcgg gcttttttt          364
Ser Lys Ala Ser
 65 tactgacatc ctcgaggcct ttctctccac agggtagat aactgaactt gtttattgca    424 ga                                                                  426
```

<210> SEQ ID NO 6
<211> LENGTH: 68
<212> TYPE: PRT
<213> ORGANISM: Artificial Sequence
<220> FEATURE:
<223> OTHER INFORMATION: Description of Artificial Sequence: pAM8

<400> SEQUENCE: 6

```
Ser Ile Gln His Phe Arg Val Ala Leu Ile Pro Phe Phe Ala Ala Phe
 1               5                  10                  15

Cys Leu Pro Val Phe Ala Gly Pro Gly Gly Trp Ala Ala Ala Glu Gln
             20                  25                  30

Lys Leu Ile Ser Glu Glu Asp Leu Ala His His His His His Leu
         35                  40                  45

Gln Pro Leu Ser Trp Gln Val Ser Ala Glu Gly Asp Asp Pro Phe Thr
     50                  55                  60

Ser Lys Ala Ser
 65
```

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence:
    Thrombospondin derived peptide

<400> SEQUENCE: 7

```
Ser Pro Trp Ser Ser Ala Ser Val Thr Cys Gly Asp Gly Val Ile Thr
 1               5                  10                  15

Arg Ile Arg
```

<210> SEQ ID NO 8
<211> LENGTH: 9
<212> TYPE: PRT
<213> ORGANISM: Artificial Sequence
<220> FEATURE:

-continued

<223> OTHER INFORMATION: Description of Artificial Sequence: RGD motif

<400> SEQUENCE: 8

Cys Asp Cys Arg Gly Asp Cys Phe Cys
 1               5